United States Patent
Kim et al.

(10) Patent No.: US 8,709,386 B2
(45) Date of Patent: Apr. 29, 2014

(54) METHOD OF MAKING AND USING AN ALPHA-GLUCANASE COMPOSITION TO REDUCE OR REMOVE BIOFILM

(75) Inventors: Steven Kim, Fremont, CA (US); Suzanne Lantz, San Carlos, CA (US); Michael Pepsin, Castro Valley, CA (US)

(73) Assignee: Danisco US Inc., Palo Alto, CA (US)

( * ) Notice: Subject to any disclaimer, the term of this patent is extended or adjusted under 35 U.S.C. 154(b) by 177 days.

(21) Appl. No.: 12/937,362

(22) PCT Filed: Apr. 9, 2009

(86) PCT No.: PCT/US2009/040013
§ 371 (c)(1), (2), (4) Date: May 26, 2011

(87) PCT Pub. No.: WO2009/126773
PCT Pub. Date: Oct. 15, 2009

(65) Prior Publication Data
US 2011/0223117 A1     Sep. 15, 2011

Related U.S. Application Data

(60) Provisional application No. 61/044,316, filed on Apr. 11, 2008.

(51) Int. Cl.
A61K 8/66 (2006.01)

(52) U.S. Cl.
USPC ......... 424/50; 424/94.2; 424/94.61; 435/200; 435/320.1; 435/243

(58) Field of Classification Search
None
See application file for complete search history.

(56) References Cited

U.S. PATENT DOCUMENTS

| | | | |
|---|---|---|---|
| 3,988,433 | A | 10/1976 | Benedict |
| 4,353,891 | A | 10/1982 | Guggenheim et al. |
| 5,578,295 | A | 11/1996 | Francis et al. |
| 6,022,725 | A | 2/2000 | Fowler et al. |
| 6,238,648 | B1 | 5/2001 | Leusch et al. |
| 6,268,328 | B1 | 7/2001 | Mitchinson et al. |
| 7,262,041 | B2 | 8/2007 | Baldwin et al. |
| 7,795,002 | B2 | 9/2010 | Davidson et al. |
| 2006/0041113 | A1 | 2/2006 | Stafford et al. |

FOREIGN PATENT DOCUMENTS

| | | |
|---|---|---|
| EP | 1207197 | 5/2002 |
| WO | WO 98/00528 | 1/1998 |
| WO | WO2006/092099 | 9/2006 |
| WO | WO2008/008617 | 1/2008 |

OTHER PUBLICATIONS

Hassane Ait-Lahsen et al. (Applied &Environmental Microbio., vo.. 67, No. 12, Dec. 2001, pp. 5833-5839).*
Hayacibara et al. (Carbohydr. Res. vol. 339, No. 12, Aug. 2004, pp. 2127-2137 (Abstract).*
Ait-Lahsen et al. (2001) *Appl. Environ. Microbiol.* 67:5833-9.
Bhikhabhai et al. (1984) *J. Appl. Biochem.* 6:336.
Boel et al. (1984) *EMBO J.* 3:1097-102.
Boel et al. (1984) *EMBO J.* 3:1581-85.
Brumbauer et al. (1999) *Bioseparation* 7:287.
Cao et al. (2000) *Protein Sci.* 9:991-1001.
Ellouz et al. (1987) *Chromatography* 396:307.
Fliess et al. (1983) *Eur. J. Appl. Microbiol. Biotechnol.* 17:314.
Fuglsang et al. (2000) *J. Biol. Chem.* 275:2009-18.
Genbank database *Aspergillus niger* (accession No. XP_001390909. 1; GID: 145236523).
Genbank database *Cryptococcus neoformans* (accession No. AAW47079.1; GID: 57230770).
Genbank database *Emericella nidulans* (accession No. CAC48025.1; GID: 15072711).
Genbank database *Penicillium purpurogenum* (accession No. AAF27912.1; GID: 6752866).
Goyal et al. (1991) *Biores. Technol.* 36:37.
Guggenheim B. et al., "Purification and Properties of an Alpha-1 Replaced by 3 Glucano Hydrolase from *Trichoderma-harzianum*," J. Dental Research, (1972) 51:2 pp. 394-402.
Innis et al. (1985) *Science* 228:21-26.
Inoue et al. (1988) *Carbohydr. Res.* 182:277-86.
ISR for PCT/US2009/040013 mailed on Sep. 15, 2009.
Lad. R. (ed.) "Biotechnology in Personal Care", *Cosmetic Science and Technology Series*, vol. 29, Taylor and Francis Group, New York, NY, USA, 2006.
Marchler-Bauer et al. CDD: a conserved domain database for interactive domain family analysis. (2007) *Nucleic Acids Res.* 35:D237-40.
Medve et al. (1998) *J. Chromatography A.* 808:153.
Nakamura et al. (2000) *Nucl. Acids Res.* 28:292.
Nevalainen et al. (1992) "The Molecular Biology of Trichoderma and its Application to the Expression of Both Homologous and Heterologous Genes" in Molecular Industrial Mycology, Eds. Leong and Berka, Marcel Dekker Inc., NY, pp. 129-148.
Nunberg et al. (1984) *Mol Cell Biol.* 4:2306-15.
Paloheimo et al. (2003) *Appl. Environ. Microbiol.* 69:7073-82.
Punt et al. (1987) *Gene* 56:117-24.
Saarelainen (1997) *Appl. Environ. Microbiol.* 63:4938-40.
Sumitomo et al. (2007) *Biochim. Biophys. Acta.* 1770:716-24.
Tomaz and Queiroz (1999) *J. Chromatography A.* 865:123.
Van Tilbeurgh et al. (1984) *FEBS Lett.* 16:215.
Yelton et al. (1984) *Proc. Natl. Acad. Sci. USA* 81:1470-74.
Druzhinina, I., et al., "Species concepts and biodiversity in Trichoderma and Hypocrea: from aggregate species to species clusters?" Journal of Zhejiang University, vol. 6B, No. 2 pp. 100-122, 2005.
Database Geneseq; Sep. 28, 1998, "Trichoderma harzianum mutanase." Retrieved from EBI Accession No. GSP:AAW60210.
European Search Report for European Patent Application No. 13165442.8 dated Aug. 30, 2013.
European Search Report for European Patent Application No. 13165441.0 dated Aug. 27, 2013.

(Continued)

*Primary Examiner* — Hope Robinson
(74) *Attorney, Agent, or Firm* — Danisco US Inc.

(57) ABSTRACT

Isolated α-glucanases from *Hypocrea tawa*, *Trichoderma reesei*, and *Trichoderma konilangbra* are described, as well as oral care compositions containing the same. The oral care composition may be employed to prevent or reduce dental plaque.

9 Claims, 3 Drawing Sheets

(56) References Cited

OTHER PUBLICATIONS

Written Opinion of the International Searching Authority for PCT/US2009/040013 mailed on Sep. 15, 2009.

International Preliminary Report on Patentability for International Application No. PCT/US2009/040013 dated Oct. 12, 2010.

Sanz, L., et al., "Expression of an α-1,3-glucanase during mycoparasitic interaction of *Trichoderma asperellum*." FEBS 272: 493-499, 2005.

* cited by examiner

FIG. 1

| | | | | | | | | |
|---|---|---|---|---|---|---|---|---|
| Majority | | RDTDXXXYVQNEQLVYWYRRNLKXLDCDATDTTSNRPANNGSNYFMGRPDGWQTMDDTVYXALLKTAGXVTVTSGGXT | | | | | | |
| | | 330 | 340 | 350 | 360 | 370 | 380 | 390 400 |
| T. reesei 592.pro | | RDTDVAPYIQNEQLIYWYRRNLKGLDCDATDTTSNRPANNGSGNYFMGRPDGWQTMDDTVYVALLKSAGTVTVTSGGAT 400 |
| T. koni consensus.pro | | RDTNVARYVQSDQLVYWYRRTLKGLDCDATDTTSNRPANNASGNYFMGRPDGWQTMDDTVYIVVALLTAAGTVTVTSGGAT 400 |
| H. tawa consensus.pro | | RDTDISKYVQNEQLVYWYRRNLKALDCDATDTTSNRPANNGSGNYFMGRPDGWQTMDDTVYVAALLKTAGSVTVTSGGTT 400 |
| T. harzianum mutA.pro | | RDTDISKYVQNEQLVYWYRRNLKALDCDATDTTSNRPANNGSGNYFMGRPDGWQTMDDTVYAALLKTAGSVTVTSGGTT 400 |

| | | | | | | | |
|---|---|---|---|---|---|---|---|
| Majority | QTFQGXAGANLFXKPAXXGQQKFALXRNGQTVFSXTSLMDITNVCXCGIYNFNPYVGTXPAGFDDPLQADGLXSLTIGLH | | | | | | |
| | 410 | 420 | 430 | 440 | 450 | 460 | 470 480 |
| T. reesei 592.pro | QTFQGTAGANLFEVPANLGQQKFALSRNGQTVFSSTSLMDITNVCPCGIYNFNPYVGTIVPAGFDDPLGPDGLASLTIGLH 480 |
| T. koni consensus.pro | QTFQGTAGANLFEVPANLGQQKFALSRNGQTVFSSTSLMDITNVCPCGLYNFNPYVGTVPPGFDDPLQADGLASLTIGLH 480 |
| H. tawa consensus.pro | QTFQGNAGANLFQIPASIGQQKFALTRNGQTVFSGTSLMDITNVCSCGIYNFNPYVGTIPAGFDDPLSLTIGLH 480 |
| T. harzianum mutA.pro | QTFQANAGANLFQIPASIGQQKFALTRNGQTVFSGTSLMDITNVCSCGIYNFNPYVGTIPAGFDDPLQADGLFSLTIGLH 480 |

Linker Domain

| | | | | | | | |
|---|---|---|---|---|---|---|---|
| Majority | VTTCQAKPSLGTNPPXTSGPXSSXPASXTXRASSPPXSXTRXSSXPVSSXXX--RXSSSXPPXXXSTPPXGQVCVAGTVA | | | | | | |
| | 490 | 500 | 510 | 520 | 530 | 540 | 550 560 |
| T. reesei 592.pro | VTTCQAKPSLGTNPPITSGPGSSVPVST------PPGSTTRFSSTPVSS------RSSSSTPF--VSTPPPGQVCVAGTVA 547 |
| T. koni consensus.pro | VTTCQAKPSLGTNPPITSGPGSSVPASTT--RSTSPPGSTSRFSTRVSS------RSISSTPF--VSTPPPGQVCVAGTVA 552 |
| H. tawa consensus.pro | VTTCQAKPSLGTNPPVTSGPVSSLPASSTTRASSPPVTSSPPVSSPPVTSRTSSSPPPASSTPSSGQVCVAGTVA 560 |
| T. harzianum mutA.pro | VTTCQAKPSLGTNPPVTSGPVSSLPASSTTRASSPPVSSPPVSSPPVS--RTSSPPPPASSTPPSGQVCVAGTVA 559 |

Glucan-binding Domain

| | | | | | | |
|---|---|---|---|---|---|---|
| Majority | DGXSGNYIGLCXFSCNXGYCPPGPCKCTAFGAPIXPPAXNGRNGCPLPGEXDXYLGLCSFSCNHNYCPPTACQYC | | | | | |
| | 570 | 580 | 590 | 600 | 610 | 620 630 |
| T. reesei 592.pro | DGQSGNYIGLCNFSCNFGYCPPGPCKCTAFGAPINPPATNGRNGCPLPGEDDSYLGLCSFSCNHNYCPPTACQYC 622 |
| T. koni consensus.pro | DGQSGNYIGLCNFSCNFGYCPPGPCKCTAFGAPINPPATNGRNGCPLPGEDDSYLGLCSFSCNHNYCPPTACQYC 627 |
| H. tawa consensus.pro | DGESGNYIGLCQFSCNYGYCPPGPCKCTAFGAPISPPASNGRNGCPLPGEGDGYLGLCSFSCNHNYCPPTACQYC 635 |
| T. harzianum mutA.pro | DGESGNYIGLCQFSCNYGYCPPGPCKCTAFGAPISPPASNGRNGCPLPGEGDGYLGLCSFSCNHNYCPPTACQYC 634 |

SEQUENCE LISTING

<160> NUMBER OF SEQ ID NOS: 34

<210> SEQ ID NO 1
<211> LENGTH: 635
<212> TYPE: PRT
<213> ORGANISM: Hypocrea tawa

<400> SEQUENCE: 1

Met Leu Gly Val Phe Arg Arg Leu Gly Leu Gly Ser Leu Ala Ala Ala
1               5                   10                  15

Ala Leu Ser Ser Leu Gly Thr Ala Ala Pro Ala Asn Val Ala Ile Arg
            20                  25                  30

```
Ser Leu Glu Glu Arg Ala Ser Ser Ala Asp Arg Leu Val Phe Cys His
     35                  40                  45
Phe Met Ile Gly Ile Val Gly Asp Arg Gly Ser Ser Ala Asp Tyr Asp
 50                  55                  60
Asp Asp Met Gln Arg Ala Lys Ala Ala Gly Ile Asp Ala Phe Ala Leu
 65                  70                  75                  80
Asn Ile Gly Val Asp Gly Tyr Thr Asp Gln Gln Leu Gly Tyr Ala Tyr
                 85                  90                  95
Asp Ser Ala Asp Arg Asn Gly Met Lys Val Phe Ile Ser Phe Asp Phe
                100                 105                 110
Asn Trp Trp Ser Pro Gly Asn Ala Val Gly Val Gly Gln Lys Ile Ala
            115                 120                 125
Gln Tyr Ala Asn Arg Pro Ala Gln Leu Tyr Val Asp Asn Arg Pro Phe
130                 135                 140
Ala Ser Ser Phe Ala Gly Asp Gly Leu Asp Val Asn Ala Leu Arg Asn
145                 150                 155                 160
Ala Ala Gly Ser Asn Val Tyr Phe Val Pro Asn Phe His Pro Gly Gln
                165                 170                 175
Ser Ser Pro Ser Asn Ile Asp Gly Ala Leu Asn Trp Met Ala Trp Asp
            180                 185                 190
Asn Asp Gly Asn Asn Lys Ala Pro Lys Gln Gly Gln Thr Val Thr Val
        195                 200                 205
Ala Asp Gly Asp Asn Ala Tyr Lys Asn Trp Leu Gly Lys Pro Tyr
210                 215                 220
Leu Ala Pro Val Ser Pro Trp Phe Phe Thr His Phe Gly Pro Glu Val
225                 230                 235                 240
Ser Tyr Ser Lys Asn Trp Val Phe Pro Gly Gly Ala Leu Ile Tyr Asn
                245                 250                 255
Arg Trp Gln Gln Val Leu Gln Gln Gly Phe Pro Met Val Glu Ile Val
            260                 265                 270
Thr Trp Asn Asp Tyr Gly Glu Ser His Tyr Val Gly Pro Leu Lys Ser
        275                 280                 285
Lys His Phe Asp Asp Gly Asn Ser Lys Trp Val Asn Asp Met Pro His
290                 295                 300
Asp Gly Phe Leu Asp Leu Ser Lys Pro Phe Ile Ala Ala Tyr Lys Asn
305                 310                 315                 320
Arg Asp Thr Asp Ile Ser Lys Tyr Val Gln Asn Glu Gln Leu Val Tyr
                325                 330                 335
Trp Tyr Arg Arg Asn Leu Lys Ala Leu Asp Cys Asp Ala Thr Asp Thr
            340                 345                 350
Thr Ser Asn Arg Pro Ala Asn Asn Gly Ser Gly Asn Tyr Phe Met Gly
        355                 360                 365
Arg Pro Asp Gly Trp Gln Thr Met Asp Asp Thr Val Tyr Val Ala Ala
370                 375                 380
Leu Leu Lys Thr Ala Gly Ser Val Thr Val Thr Ser Gly Gly Thr Thr
385                 390                 395                 400
Gln Thr Phe Gln Gly Asn Ala Gly Ala Asn Leu Phe Gln Ile Pro Ala
                405                 410                 415
Ser Ile Gly Gln Gln Lys Phe Ala Leu Thr Arg Asn Gly Gln Thr Val
            420                 425                 430
Phe Ser Gly Thr Ser Leu Met Asp Ile Thr Asn Val Cys Ser Cys Gly
        435                 440                 445
Ile Tyr Asn Phe Asn Pro Tyr Val Gly Thr Ile Pro Ala Gly Phe Asp
450                 455                 460
```

```
Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
            500                 505                 510

Ser Ser Pro Pro Val Ser Ser Thr Arg Val Ser Ser Pro Pro Val Ser
        515                 520                 525

Ser Pro Pro Val Thr Ser Arg Thr Ser Ser Pro Pro Pro Ala
    530                 535                 540

Ser Ser Thr Pro Ser Ser Gly Gln Val Cys Val Ala Gly Thr Val Ala
545                 550                 555                 560

Asp Gly Glu Ser Gly Asn Tyr Ile Gly Leu Cys Gln Phe Ser Cys Asn
                565                 570                 575

Tyr Gly Tyr Cys Pro Pro Gly Pro Cys Lys Cys Thr Ala Phe Gly Ala
            580                 585                 590

Pro Ile Ser Pro Pro Ala Ser Asn Gly Arg Asn Gly Cys Pro Leu Pro
        595                 600                 605

Gly Glu Gly Asp Gly Tyr Leu Gly Leu Cys Ser Phe Ser Cys Asn His
    610                 615                 620

Asn Tyr Cys Pro Pro Thr Ala Cys Gln Tyr Cys
625                 630                 635

<210> SEQ ID NO 2
<211> LENGTH: 622
<212> TYPE: PRT
<213> ORGANISM: Trichoderma reesei

<400> SEQUENCE: 2

Met Phe Gly Leu Val Arg Arg Leu Gly Val Gly Ala Leu Val Ala Ala
1               5                   10                  15

Ala Leu Ser Ser Leu Ala Ala Ala Pro Ala Asn Val Ala Ile Arg
                20                  25                  30

Ser Leu Glu Glu Arg Ala Ser Ala Asp Arg Leu Val Phe Cys His
            35                  40                  45

Phe Met Ile Gly Ile Cys Gly Asp Arg Thr Ser Ser Thr Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Asn Phe Ala Tyr
                85                  90                  95

Asp Ala Ala Asp Arg Ala Gly Met Lys Val Phe Ile Ser Phe Asp Phe
            100                 105                 110

Asn Trp Trp Ser Pro Gly Asn Ala Ala Gly Val Gly Gln Lys Ile Ala
        115                 120                 125

Gln Tyr Ala Ser Arg Pro Ala Gln Leu Tyr Val Asp Asn Arg Pro Phe
    130                 135                 140

Ala Ser Ser Phe Ala Gly Asp Gly Leu Asp Val Asn Thr Leu Arg Asn
145                 150                 155                 160

Ala Ala Gly Ser Asn Val Tyr Phe Val Pro Asn Phe His Pro Gly Gln
                165                 170                 175

Ser Ser Pro Ser Thr Ile Asp Gly Ala Leu Asn Trp Met Ala Trp Asp
            180                 185                 190

Asn Asp Gly Asn Asn Lys Ala Pro Lys Pro Gly Gln Asn Val Thr Val
        195                 200                 205
```

-continued

Ala Asp Gly Asp Asn Ser Tyr Arg Ser Trp Leu Ala Gly Lys Pro Tyr
            210                 215                 220
Leu Ala Pro Val Ser Pro Trp Phe Phe Thr His Phe Gly Pro Glu Val
225                 230                 235                 240
Ser Tyr Ser Lys Asn Trp Val Phe Pro Gly Gly Ser Leu Trp Tyr Asp
                    245                 250                 255
Arg Trp Gln Asp Val Leu Arg Gln Gly Phe Glu Met Val Glu Ile Val
                260                 265                 270
Thr Trp Asn Asp Tyr Gly Glu Ser His Tyr Thr Gly Pro Leu Glu Ser
            275                 280                 285
Arg His Tyr Asp Asp Gly Asn Ser Lys Trp Thr Asn Asp Met Pro His
        290                 295                 300
Asp Gly Phe Leu Asp Leu Ala Lys Pro Phe Ile Ala Ala Tyr Lys Asn
305                 310                 315                 320
Arg Asp Thr Asp Val Ala Pro Tyr Ile Gln Asn Glu Gln Leu Ile Tyr
                    325                 330                 335
Trp Tyr Arg Arg Asn Leu Lys Gly Leu Asp Cys Asp Ala Thr Asp Thr
                340                 345                 350
Thr Ser Asn Arg Pro Ala Asn Asn Gly Ser Gly Asn Tyr Phe Met Gly
            355                 360                 365
Arg Pro Asp Gly Trp Gln Thr Met Asp Asp Thr Val Tyr Val Val Ala
        370                 375                 380
Leu Leu Lys Ser Ala Gly Thr Val Thr Val Thr Ser Gly Gly Ala Thr
385                 390                 395                 400
Gln Thr Phe Gln Gly Thr Ala Gly Ala Asn Leu Phe Glu Val Pro Ala
                    405                 410                 415
Asn Leu Gly Gln Gln Lys Phe Ala Leu Ser Arg Asn Gly Gln Thr Val
                420                 425                 430
Phe Ser Ser Thr Ser Leu Met Asp Ile Thr Asn Val Cys Pro Cys Gly
            435                 440                 445
Ile Tyr Asn Phe Asn Pro Tyr Val Gly Thr Val Pro Ala Gly Phe Asp
        450                 455                 460
Asp Pro Leu Gly Pro Asp Gly Leu Ala Ser Leu Thr Ile Gly Leu His
465                 470                 475                 480
Val Thr Thr Cys Gln Ala Lys Pro Ser Leu Gly Thr Asn Pro Pro Ile
                    485                 490                 495
Thr Ser Gly Pro Gly Ser Ser Val Pro Val Ser Thr Pro Pro Gly Ser
                500                 505                 510
Thr Thr Arg Phe Ser Ser Thr Pro Val Ser Ser Arg Ser Ser Ser Ser
            515                 520                 525
Thr Pro Pro Val Ser Thr Pro Pro Gly Gln Val Cys Val Ala Gly
        530                 535                 540
Thr Val Ala Asp Gly Gln Ser Gly Asn Tyr Ile Gly Leu Cys Asn Phe
545                 550                 555                 560
Ser Cys Asn Phe Gly Tyr Cys Pro Pro Gly Pro Cys Lys Cys Thr Ala
                    565                 570                 575
Tyr Gly Ala Pro Ile Asn Pro Pro Ala Thr Asn Gly Arg Asn Gly Cys
                580                 585                 590
Pro Leu Pro Gly Glu Asp Asp Ser Tyr Leu Gly Leu Cys Ser Phe Ser
            595                 600                 605
Cys Asn His Asn Tyr Cys Pro Pro Thr Ala Cys Gln Tyr Cys
        610                 615                 620

```
<210> SEQ ID NO 3
<211> LENGTH: 627
<212> TYPE: PRT
<213> ORGANISM: Trichoderma konilangbra

<400> SEQUENCE: 3

Met Leu Gly Ile Leu Arg Arg Leu Ala Leu Gly Ala Leu Ala Ala Ala
1               5                   10                  15

Ala Leu Ser Pro Leu Val Val Ala Ala Pro Ala Asn Val Ala Ile Arg
            20                  25                  30

Ser Leu Glu Glu Arg Ala Ser Ser Ala Asp Arg Leu Val Phe Cys His
        35                  40                  45

Phe Met Ile Gly Ile Cys Gly Asp Arg Gly Ser Ser Thr Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Asn Phe Ala Tyr
                85                  90                  95

Asp Ala Ala Asp Arg Ala Gly Met Lys Val Phe Ile Ser Phe Asp Phe
            100                 105                 110

Asn Trp Trp Ser Pro Gly Asn Ala Val Gly Val Gly Gln Lys Ile Ala
        115                 120                 125

Gln Tyr Ala Ser Arg Pro Ala Gln Leu Tyr Val Asp Asn Arg Pro Phe
    130                 135                 140

Ala Ser Ser Phe Ala Gly Asp Gly Leu Asp Val Asn Ala Leu Arg Asn
145                 150                 155                 160

Ala Ala Gly Ser Asn Val Tyr Phe Val Pro Asn Phe His Pro Gly Gln
                165                 170                 175

Ser Ser Pro Ser Thr Ile Asp Gly Ala Leu Asn Trp Met Ala Trp Asp
            180                 185                 190

Asn Asp Gly Asn Asn Lys Ala Pro Lys Pro Gly Arg Asn Val Thr Val
        195                 200                 205

Ala Asp Gly Asp Asn Ser Tyr Arg Ser Trp Leu Gly Gly Lys Pro Tyr
    210                 215                 220

Leu Ala Pro Val Ser Pro Trp Phe Phe Thr His Phe Gly Pro Glu Val
225                 230                 235                 240

Ser Phe Ser Lys Asn Trp Val Phe Pro Gly Gly Ser Leu Leu Tyr Asp
                245                 250                 255

Arg Trp Gln Asp Val Leu Arg Gln Gly Pro Glu Met Val Glu Ile Ile
            260                 265                 270

Thr Trp Asn Asp Tyr Gly Glu Ser His Tyr Thr Gly Pro Leu Lys Ser
        275                 280                 285

Arg His Tyr Asp Asp Gly Asn Ser Lys Trp Thr Asn Asp Met Pro His
    290                 295                 300

Asp Gly Phe Leu Asp Leu Ser Lys Pro Phe Ile Ala Ala Tyr Lys Asn
305                 310                 315                 320

Arg Asp Thr Asn Val Ala Arg Tyr Val Gln Ser Asp Gln Leu Val Tyr
                325                 330                 335

Trp Tyr Arg Arg Thr Leu Lys Gly Leu Asp Cys Asp Ala Thr Asp Thr
            340                 345                 350

Thr Ser Asn Arg Pro Ala Asn Asn Ala Ser Gly Asn Tyr Phe Met Gly
        355                 360                 365

Arg Pro Asp Gly Trp Gln Thr Met Asp Asp Thr Val Tyr Val Val Ala
    370                 375                 380

Leu Leu Thr Ala Ala Gly Thr Val Thr Val Thr Ser Gly Gly Ala Thr
```

```
            385                 390                 395                 400
Gln Thr Phe Gln Gly Thr Ala Gly Ala Asn Leu Phe Glu Val Pro Ala
                    405                 410                 415

Asn Leu Gly Gln Gln Lys Phe Ala Leu Ser Arg Asn Gly Gln Thr Val
            420                 425                 430

Phe Ser Ser Thr Ser Leu Met Asp Ile Ala Asn Val Cys Pro Cys Gly
            435                 440                 445

Leu Tyr Asn Phe Asn Pro Tyr Val Gly Thr Val Pro Pro Gly Phe Asp
    450                 455                 460

Asp Pro Leu Gln Ala Asp Gly Leu Ala Ser Leu Thr Ile Gly Leu His
465                 470                 475                 480

Val Thr Thr Cys Gln Ala Arg Pro Ser Leu Gly Thr Asn Pro Pro Ile
                485                 490                 495

Thr Ser Gly Pro Gly Ser Ser Val Pro Ala Ser Thr Thr Arg Ser Thr
                500                 505                 510

Ser Pro Pro Gly Ser Thr Ser Arg Phe Ser Ser Thr Pro Val Ser Ser
            515                 520                 525

Arg Ser Ile Ser Ser Thr Pro Pro Val Ser Thr Pro Pro Gly Gln
    530                 535                 540

Val Cys Val Ala Gly Thr Val Ala Asp Gly Gln Ser Gly Asn Tyr Ile
545                 550                 555                 560

Gly Leu Cys Asn Phe Ser Cys Asn Phe Gly Tyr Cys Pro Pro Gly Pro
                565                 570                 575

Cys Lys Cys Thr Ala Phe Gly Ala Pro Ile Asn Pro Pro Ala Thr Asn
                580                 585                 590

Gly Arg Asn Gly Cys Pro Leu Pro Gly Glu Asp Asp Ser Tyr Leu Gly
                595                 600                 605

Leu Cys Ser Phe Ser Cys Asn His Asn Tyr Cys Pro Pro Thr Ala Cys
    610                 615                 620

Gln Tyr Cys
625

<210> SEQ ID NO 4
<211> LENGTH: 634
<212> TYPE: PRT
<213> ORGANISM: Trichoderma harzianum

<400> SEQUENCE: 4

Met Leu Gly Val Val Arg Arg Leu Gly Leu Gly Ala Leu Ala Ala Ala
1               5                   10                  15

Ala Leu Ser Ser Leu Gly Ser Ala Ala Pro Ala Asn Val Ala Ile Arg
            20                  25                  30

Ser Leu Glu Glu Arg Ala Ser Ser Ala Asp Arg Leu Val Phe Cys His
        35                  40                  45

Phe Met Ile Gly Ile Val Gly Asp Arg Gly Ser Ala Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95

Asp Ser Ala Asp Arg Asn Gly Met Lys Val Phe Ile Ser Phe Asp Phe
            100                 105                 110

Asn Trp Trp Ser Pro Gly Asn Ala Val Gly Val Gly Gln Lys Ile Ala
        115                 120                 125

Gln Tyr Ala Ser Arg Pro Ala Gln Leu Tyr Val Asp Asn Arg Pro Phe
```

```
              130                 135                 140
Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
                180                 185                 190

Asn Asp Gly Asn Asn Lys Ala Pro Lys Pro Gly Gln Thr Val Thr Val
                195                 200                 205

Ala Asp Gly Asp Asn Ala Tyr Lys Asn Trp Leu Gly Gly Lys Pro Tyr
210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Pro Leu Ile Tyr Asn
                245                 250                 255

Arg Trp Gln Gln Val Leu Gln Gln Gly Phe Pro Met Val Glu Ile Val
                260                 265                 270

Thr Trp Asn Asp Tyr Gly Glu Ser His Tyr Val Gly Pro Leu Lys Ser
                275                 280                 285

Lys His Phe Asp Asp Gly Asn Ser Lys Trp Val Asn Asp Met Pro His
                290                 295                 300

Asp Gly Phe Leu Asp Leu Ser Lys Pro Phe Ile Ala Ala Tyr Lys Asn
305                 310                 315                 320

Arg Asp Thr Asp Ile Ser Lys Tyr Val Gln Asn Glu Gln Leu Val Tyr
                325                 330                 335

Trp Tyr Arg Arg Asn Leu Lys Ala Leu Asp Cys Asp Ala Thr Asp Thr
                340                 345                 350

Thr Ser Asn Arg Pro Ala Asn Asn Gly Ser Gly Asn Tyr Phe Met Gly
                355                 360                 365

Arg Pro Asp Gly Trp Gln Thr Met Asp Asp Thr Val Tyr Val Ala Ala
                370                 375                 380

Leu Leu Lys Thr Ala Gly Ser Val Thr Val Thr Ser Gly Gly Thr Thr
385                 390                 395                 400

Gln Thr Phe Gln Ala Asn Ala Gly Ala Asn Leu Phe Gln Ile Pro Ala
                405                 410                 415

Ser Ile Gly Gln Gln Lys Phe Ala Leu Thr Arg Asn Gly Gln Thr Val
                420                 425                 430

Phe Ser Gly Thr Ser Leu Met Asp Ile Thr Asn Val Cys Ser Cys Gly
                435                 440                 445

Ile Tyr Asn Phe Asn Pro Tyr Val Gly Thr Ile Pro Ala Gly Phe Asp
                450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
                500                 505                 510

Ser Ser Pro Pro Val Ser Ser Thr Arg Val Ser Ser Pro Pro Val Ser
                515                 520                 525

Ser Pro Pro Val Ser Arg Thr Ser Ser Pro Pro Pro Pro Ala Ser
                530                 535                 540

Ser Thr Pro Pro Ser Gly Gln Val Cys Val Ala Gly Thr Val Ala Asp
545                 550                 555                 560
```

```
Gly Glu Ser Gly Asn Tyr Ile Gly Leu Cys Gln Phe Ser Cys Asn Tyr
                565                 570                 575

Gly Tyr Cys Pro Pro Gly Pro Cys Lys Cys Thr Ala Phe Gly Ala Pro
            580                 585                 590

Ile Ser Pro Pro Ala Ser Asn Gly Arg Asn Gly Cys Pro Leu Pro Gly
        595                 600                 605

Glu Gly Asp Gly Tyr Leu Gly Leu Cys Ser Phe Ser Cys Asn His Asn
    610                 615                 620

Tyr Cys Pro Pro Thr Ala Cys Gln Tyr Cys
625                 630

<210> SEQ ID NO 5
<211> LENGTH: 633
<212> TYPE: PRT
<213> ORGANISM: Artificial Sequence
<220> FEATURE:
<223> OTHER INFORMATION: synthetic consensus sequence
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
```

```
<222> LOCATION: (283)..(283)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (325)..(326)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (406)..(406)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (417)..(418)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (435)..(435)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
```

-continued

```
<222> LOCATION: (508)..(508)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (522)..(522)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (530)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (538)..(538)
<223> OTHER INFORMATION: Xaa can be any naturally occurring amino acid
<220> FEATURE:
<221> NAME/KEY: misc_feature
<222> LOCATION: (541)..(543)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (561)..(561)
<223> OTHER INFORMATION: Xaa can be any naturally occurring amino acid
<220> FEATURE:
<221> NAME/KEY: misc_feature
<222> LOCATION: (570)..(570)
<223> OTHER INFORMATION: Xaa can be any naturally occurring amino acid
<220> FEATURE:
<221> NAME/KEY: misc_feature
<222> LOCATION: (575)..(575)
<223> OTHER INFORMATION: Xaa can be any naturally occurring amino acid
<220> FEATURE:
<221> NAME/KEY: misc_feature
<222> LOCATION: (593)..(593)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid
<220> FEATURE:
<221> NAME/KEY: misc_feature
<222> LOCATION: (609)..(609)
<223> OTHER INFORMATION: Xaa can be any naturally occurring amino acid
<220> FEATURE:
<221> NAME/KEY: misc_feature
<222> LOCATION: (611)..(611)
<223> OTHER INFORMATION: Xaa can be any naturally occurring amino acid

<400> SEQUENCE: 5

Met Leu Gly Val Val Arg Arg Leu Gly Leu Gly Ala Leu Ala Ala Ala
1               5                   10                  15

Ala Leu Ser Ser Leu Gly Xaa Ala Ala Pro Ala Asn Val Ala Ile Arg
            20                  25                  30

Ser Leu Glu Glu Arg Ala Ser Ser Ala Asp Arg Leu Val Phe Cys His
```

```
                35                  40                  45
Phe Met Ile Gly Ile Xaa Gly Asp Arg Gly Ser Ser Xaa Asp Tyr Asp
 50                  55                  60

Asp Asp Met Gln Arg Ala Lys Ala Ala Gly Ile Asp Ala Phe Ala Leu
 65                  70                  75                  80

Asn Ile Gly Val Asp Gly Tyr Thr Asp Gln Gln Leu Xaa Xaa Ala Tyr
                 85                  90                  95

Asp Xaa Ala Asp Arg Xaa Gly Met Lys Val Phe Ile Ser Phe Asp Phe
                100                 105                 110

Asn Trp Trp Ser Pro Gly Asn Ala Val Gly Val Gly Gln Lys Ile Ala
                115                 120                 125

Gln Tyr Ala Ser Arg Pro Ala Gln Leu Tyr Val Asp Asn Arg Pro Phe
                130                 135                 140

Ala Ser Ser Phe Ala Gly Asp Gly Leu Asp Val Asn Ala Leu Arg Asn
145                 150                 155                 160

Ala Ala Gly Ser Asn Val Tyr Phe Val Pro Asn Phe His Pro Gly Gln
                165                 170                 175

Ser Ser Pro Ser Xaa Ile Asp Gly Ala Leu Asn Trp Met Ala Trp Asp
                180                 185                 190

Asn Asp Gly Asn Asn Lys Ala Pro Lys Pro Gly Gln Xaa Val Thr Val
                195                 200                 205

Ala Asp Gly Asp Asn Xaa Tyr Xaa Xaa Trp Leu Gly Gly Lys Pro Tyr
210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Ser Leu Ile Tyr Xaa
                245                 250                 255

Arg Trp Gln Xaa Val Leu Xaa Gln Gly Phe Xaa Met Val Glu Ile Val
                260                 265                 270

Thr Trp Asn Asp Tyr Gly Glu Ser His Tyr Xaa Gly Pro Leu Lys Ser
                275                 280                 285

Xaa His Xaa Asp Asp Gly Asn Ser Lys Trp Xaa Asn Asp Met Pro His
290                 295                 300

Asp Gly Phe Leu Asp Leu Ser Lys Pro Phe Ile Ala Ala Tyr Lys Asn
305                 310                 315                 320

Arg Asp Thr Asp Xaa Xaa Lys Tyr Val Gln Asn Glu Gln Leu Val Tyr
                325                 330                 335

Trp Tyr Arg Arg Asn Leu Lys Xaa Leu Asp Cys Asp Ala Thr Asp Thr
                340                 345                 350

Thr Ser Asn Arg Pro Ala Asn Asn Gly Ser Gly Asn Tyr Phe Met Gly
                355                 360                 365

Arg Pro Asp Gly Trp Gln Thr Met Asp Asp Thr Val Tyr Val Xaa Ala
                370                 375                 380

Leu Leu Lys Thr Ala Gly Xaa Val Thr Val Thr Ser Gly Gly Xaa Thr
385                 390                 395                 400

Gln Thr Phe Gln Gly Xaa Ala Gly Ala Asn Leu Phe Xaa Xaa Pro Ala
                405                 410                 415

Xaa Xaa Gly Gln Gln Lys Phe Ala Leu Xaa Arg Asn Gly Gln Thr Val
                420                 425                 430

Phe Ser Xaa Thr Ser Leu Met Asp Ile Thr Asn Val Cys Xaa Cys Gly
                435                 440                 445

Ile Tyr Asn Phe Asn Pro Tyr Val Gly Thr Xaa Pro Ala Gly Phe Asp
                450                 455                 460
```

```
Asp Pro Leu Gln Ala Asp Gly Leu Xaa Ser Leu Thr Ile Gly Leu His
465                 470                 475                 480

Val Thr Thr Cys Gln Ala Lys Pro Ser Leu Gly Thr Asn Pro Pro Xaa
            485                 490                 495

Thr Ser Gly Pro Xaa Ser Ser Xaa Pro Ala Ser Xaa Thr Xaa Arg Ala
        500                 505                 510

Ser Ser Pro Pro Xaa Ser Xaa Thr Arg Xaa Ser Ser Xaa Pro Val Ser
            515                 520                 525

Ser Xaa Xaa Xaa Arg Xaa Ser Ser Ser Xaa Pro Pro Xaa Xaa Xaa Ser
        530                 535                 540

Thr Pro Pro Xaa Gly Gln Val Cys Val Ala Gly Thr Val Ala Asp Gly
545                 550                 555                 560

Xaa Ser Gly Asn Tyr Ile Gly Leu Cys Xaa Phe Ser Cys Asn Xaa Gly
                565                 570                 575

Tyr Cys Pro Pro Gly Pro Cys Lys Cys Thr Ala Phe Gly Ala Pro Ile
            580                 585                 590

Xaa Pro Pro Ala Xaa Asn Gly Arg Asn Gly Cys Pro Leu Pro Gly Glu
        595                 600                 605

Xaa Asp Xaa Tyr Leu Gly Leu Cys Ser Phe Ser Cys Asn His Asn Tyr
610                 615                 620

Cys Pro Pro Thr Ala Cys Gln Tyr Cys
625                 630

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
caccatgttt ggtcttgtcc gc                                      22

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
tcagcagtac tggcatgctg                                         20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n is a, c, g, or t

<400> SEQUENCE: 8
gtnttytgyc ayttyatgat                                         20

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 9
gtnttytgyc ayttyatgat hggnat                                              26

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
gaytaygayg aygayatgca rcg                                                 23

<210> SEQ ID NO 11
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (21)..(21)
<223> OTHER INFORMATION: n is inosine
<220> FEATURE:
<221> NAME/KEY: misc_feature
<222> LOCATION: (30)..(30)
<223> OTHER INFORMATION: n is a, c, g, or t

<400> SEQUENCE: 11
gtrcayttrc anggnccngg nggrcartan cc                                       32

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
```

```
<220> FEATURE:
<221> NAME/KEY: misc_feature
<222> LOCATION: (19)..(19)
<223> OTHER INFORMATION: n is a, c, g, or t

<400> SEQUENCE: 12
ytcnccnggn agnggrcanc crtt                                          24

<210> SEQ ID NO 13
<211> LENGTH: 30
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (13)..(13)
<223> OTHER INFORMATION: n is inosine

<400> SEQUENCE: 13
rcartaytgr cangcygtyg gyggrcarta                                    30

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14 cccccctggcc aagtatgtgt                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gtacgcaaag ttgagctgct                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
agcacatcgc tgatggatat                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
aagtatacgt tgcttccggc                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 18
ctgacgatcg gactrcacgt                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
ggttgtcgac gtagagctgt                                              20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
acgatcggca gagtcatagg                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
atcggattgc atgtcacgac                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
tacatccaga ccgtcaccag                                              20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
acgtttgctc ttgcggtatc                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
tcattatccc aggcctaaaa                                              20

<210> SEQ ID NO 25
<211> LENGTH: 21

```
<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
caccatgcta ggcattctcc g                                        21

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
tcagcagtat tggcatgccg                                          20

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
caccatgttg ggcgttttc g                                         21

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
ctagcagtat tgrcatgccg                                          20

<210> SEQ ID NO 29
<211> LENGTH: 2145
<212> TYPE: DNA
<213> ORGANISM: Hypocrea tawa

<400> SEQUENCE: 29
atgttgggcg ttttcgccg cctcgggctc ggctcccttg ccgccgcagc tctgtcttct      60
ctcggcactg ccgctcccgc caatgttgct attcggtctc tcgaggaacg tgcttcttct     120
gccgaccgtc tcgtattctg tcacttcatg gttagtgttt atttacgaag tatcagaatc     180
aggactaaca tggcattttc atgacagatt ggtattgttg gtgaccgtgg cagctcggca     240
gactatgatg atgatatgca acgtgccaaa gccgctggca ttgacgcctt cgctctgaat     300
atcggcgttg acggctatac cgaccagcag cttgggtatg cctatgactc tgccgatcgt     360
aatggcatga aagtcttcat ttcattcgat ttcaattggt ggagccccgg caatgcagtt     420
ggtgttggcc agaagattgc gcagtatgcc aaccgtcccg cccagctata tgtcgataac     480
cgtccattcg cctcttcctt cgctggtgac ggtctgatt aaatgcgtt gcgcaatgct      540 gcaggctcca acgtttactt tgtgcccaac ttccaccctg gtcaatcttc tccctcaaac     600
attgacggcg ccctgaactg gatggtaagt tgcaactgca gagctgagag taggaaagca     660
aactgatgtg ttttaggcc tgggataatg atggaaacaa caaggcaccc aagcaaggcc     720
agacagtcac ggtggcagac ggcgacaacg cctacaagaa ttggttaggt ggcaagcctt    780
acctagcacc tgtctcacct tggttttttca cccatttcgg ccccgaagtt tcatattcca     840
```

```
agaactgggt tttcccaggt ggtgctctga tctataaccg gtggcaacag gtcttgcagc    900
aaggcttccc catggttgag attgttacat ggaatgacta cggcgagtct cactacgtcg    960
gcccacttaa gtctaagcat tcgacgatg gcaactccaa atgggtcaat gatatgcccc    1020
atgatggatt cctggatctt tcaaagccgt tcattgctgc ttataagaac agggatactg   1080
acatctccaa gtatgttcag aatgagcagc ttgtctactg gtaccgccgc aacttaaagg    1140
cactggactg cgacgccacc gacaccacct ctaaccgccc ggctaataat ggaagcggta    1200
attactttat gggacgccct gatggttggc aaaccatgga tgatactgtt tatgttgccg    1260
cacttctcaa gactgccggt tctgttacgg tcacgtctgg cggcaccact caaacgttcc    1320
agggcaacgc cggagccaac ctcttccaaa tcccagccag catcggccag caaaagtttg    1380
ctctaactcg taacggtcag accgtcttta gcggaacctc attgatggat atcaccaacg    1440
tttgctcttg cggtatctac aacttcaacc catatgtggg taccattcct gccggcttcg    1500
acgaccctct tcaggctgac ggtctttttct ctttgaccat cggattgcat gtcacgactt    1560
gtcaggccaa gccatctctt ggaaccaatc ctcctgtcac ttctggccct gtgtcctcgc    1620
ttccagcttc ctccactacc cgcgcatcct cgcctcctgt ttcttcaact cgcgtctctt    1680 cccccctgt ctcttcccct ccagttactt ctcgcacctc ttcttctcct ccccctccgg    1740
ccagcagcac gccgtcatcg ggtcaggttt gcgttgccgg aaccgttgct gacggcgagt    1800
ctggcaacta catcggcctg tgccaattca gctgcaagta ggttgccccc atacccctta    1860
cttgttttct taactaatcc tttgtagcta cggttactgc ccaccaggac cgtgcaagtg    1920
caccgccttt ggcgctccca tctcgccacc ggcaagcaat gggcgcaatg gctgccctct    1980
accgggcgaa ggagatggtt atctgggcct gtgcagtttc agttgtaacc ataattactg    2040 cccccaacg gcatgccaat actgctagaa gggtgggcgc gccgacccag ctttcttgta    2100
caaagttggc attataagaa agcattgctt atcaatttgt tgcaa                   2145
```

<210> SEQ ID NO 30
<211> LENGTH: 1908
<212> TYPE: DNA
<213> ORGANISM: Hypocrea tawa

<400> SEQUENCE: 30

```
atgttgggcg ttttttcgccg cctcgggctc ggctcccttg ccgccgcagc tctgtcttct    60
ctcggcactg ccgctcccgc caatgttgct attcggtctc tcgaggaacg tgcttccttct    120 gccgaccgtc tcgtattctg tcacttcatg attggtattg ttggtgaccg tggcagctcg    180
gcagactatg atgatgatat gcaacgtgcc aaagccgctg gcattgacgc cttcgctctg    240
aatatcggcg ttgacggcta taccgaccag cagcttgggt atgcctatga ctctgccgat    300
cgtaatggca tgaaagtctt catttcattc gatttcaatt ggtggagccc cggcaatgca    360
gttggtgttg gccagaagat tgcgcagtat gccaaccgtc ccgcccagct atatgtcgat    420
aaccgtccat tcgcctcttc cttcgctggt gacggtctgg atgtaaatgc gttgcgcaat    480
gctgcaggct ccaacgtttta ctttgtgccc aacttccacc ctggtcaatc ttctccctca    540
aacattgacg gcgccctgaa ctggatggcc tgggataatg atggaaacaa caaggcaccc    600
aagcaaggcc agacagtcac ggtggcagac ggcgacaacc cctacaagaa ttggttaggt    660
ggcaagcctt acctagcacc tgtctcacct tggttttttca cccatttcgg cccgaagtt    720 tcatattcca agaactgggt tttcccaggt ggtgctctga tctataaccg gtggcaacag    780
gtcttgcagc aaggcttccc catggttgag attgttacat ggaatgacta cggcgagtct    840
```

-continued

```
cactacgtcg gcccacttaa gtctaagcat ttcgacgatg gcaactccaa atgggtcaat      900
gatatgcccc atgatggatt cctggatctt tcaaagccgt tcattgctgc ttataagaac      960
agggatactg acatctccaa gtatgttcag aatgagcagc ttgtctactg gtaccgccgc     1020
aacttaaagg cactggactg cgacgccacc gacaccacct ctaaccgccc ggctaataat     1080
ggaagcggta attactttat gggacgcccc gatggttggc aaaccatgga tgatactgtt     1140
tatgttgccg cacttctcaa gactgccggt tctgttacgg tcacgtctgg cggcaccact     1200
caaacgttcc agggcaacgc cggagccaac ctcttccaaa tcccagccag catcggccag     1260
caaaagtttg ctctaactcg taacggtcag accgtcttta gcggaacctc attgatggat     1320
atcaccaacg tttgctcttg cggtatctac aacttcaacc catatgtggg taccattcct     1380
gccggcttcg acgaccctct tcaggctgac ggtcttttct ctttgaccat cggattgcat     1440
gtcacgactt gtcaggccaa gccatctctt ggaaccaatc ctcctgtcac ttctggccct     1500
gtgtcctcgc ttccagcttc ctccactacc cgcgcatcct cgcctcctgt ttcttcaact     1560
cgcgtctctt cccccctgt ctcttcccct ccagttactt ctcgcacctc ttcttctcct     1620
ccccctccgg ccagcagcac gccgtcatcg ggtcaggttt gcgttgccgg aaccgttgct     1680
gacggcgagt ctggcaacta catcggcctg tgccaattca gctgcaacta cggttactgc     1740
ccaccaggac cgtgcaagtg caccgccttt ggcgctccca tctcgccacc ggcaagcaat     1800
gggcgcaatg gctgccctct accgggcgaa ggagatggtt atctgggcct gtgcagtttc     1860
agttgtaacc ataattactg cccccaacg gcatgccaat actgctag                    1908
```

<210> SEQ ID NO 31
<211> LENGTH: 2063
<212> TYPE: DNA
<213> ORGANISM: Trichoderma reesei

<400> SEQUENCE: 31

```
atgtttggtc ttgtccgccg actcggggtc ggcgcccttg tcgccgcagc cctttcctcc       60
ctcgctgccg ccgcgccagc caacgtcgcc atccgctccc tcgaggaacg ggctagcagc      120
gcagatagac ttgtgttttg ccactttatg gtgcgtttgt ccgccccaag agcattgaaa      180
attcagtaat cactgacacg ccttactcgt gatgctagat tgggatatgt ggtgatcgca      240
cctccagtac cgattatgat gatgatatgc agcgagccaa ggccgcgggc attgacgcct      300
ttgcccttaa cattggtgtc gacggataca cggaccagca gctcaacttt gcctacgacg      360
ccgctgatcg cgccgggatg aaggtgttca tctcctttga cttcaactgg tggagccccg      420
gcaacgcggc aggcgtcggc cagaagattg cccaatatgc gtcgcggccc gcacagctct      480
acgtcgacaa ccgtcccttt gcatcgtcgt ttgccggtga cggccttgac gtgaatacgc      540
tgcggaatgc ggccggcagc aacgtgtact ttgtgcccaa cttccacccc gggcagtcgt      600
cgccgtccac catcgacggg gctctgaact ggatggtacg tctgggcgtt gtggctcgag      660
gataaagcaa agaccaagta ctcatgcgct gacacgctcc acaggcctgg acaacgacg      720 gcaacaacaa ggccccaag cccggccaaa acgtcacagt cgccgacggc gacaactcct      780
accgcagctg gctcgccggc aagccctacc tcgcccccgt ctcgccctgg ttcttcaccc      840
acttcggccc agaggtatcg tacagtaaga actgggtctt cctggcggc tccctgtggt      900 acgaccgctg gcaggacgtg ctgccaggg gcttcgagat ggtcgaaatc gtcacctgga      960
acgattacgt tgagagccac tacacggggc ccctggaaag tcgacactat gacgacggaa     1020
actcgaaatg gaccaacgac atgccgcacg acggcttcct ggacctggcg aagccattca     1080
```

```
ttgccgcgta caagaaccgc gacacggacg tggcgcccta catccagaat gagcagctga   1140
tctactggta tcggcggaat ctcaaggggc tggactgcga cgcgaccgac acgacgtcga   1200
accgcccggc gaacaacggc agcggcaact acttcatggg tcggcccgac gggtggcaga   1260
cgatggacga cacggtgtat gtggtggcgc tgctcaagag cgcgggcacg gtgacggtga   1320
cgtcgggcgg cgccacgcag acgttccagg caccgccgg cgccaacctg ttcgaggtcc   1380
cagccaacct tgggcagcag aagtttgccc tgtcccgcaa cgggcagacc gtcttcagca   1440
gcacgtcgct gatggatatc accaatgtgt gcccgtgcgg catctacaac ttcaacccgt   1500
atgtcgggac tgtgcccgct ggctttgacg acccgctcgg gcccgatggc cttgcttctt   1560
tgacaatcgg actgcacgtc acgacttgtc aggccaagcc gtcgctgggg accaacccgc   1620
ccatcacttc cggccccggc tcctcggtgc ccgtttccac tccgcccggt tccacgaccc   1680
gcttctcgtc aacgccggtt tcatctcgct ccagctcgtc cacgccgccg gttagcacgc   1740
cgccgcctgg ccaagtctgt gtcgccggta cggtggctga cggccagtcc ggcaactata   1800
ttggcctctg caacttcagc tgcaagtaag ttaccccatg tctcatgacg atgtatctcc   1860
gacaccagct aacgtttgcc agcttcgggt actgtccccc cggaccctgc aagtgcactg   1920
cctacggcgc tccgatcaac ccaccagcaa cgaatgggcg aaatgggtgc cccttgcctg   1980
gagaagacga tagttatctg ggcctctgca gcttcagctg caaccacaat tactgtccgc   2040
caacagcatg ccagtactgc tga                                          2063

<210> SEQ ID NO 32
<211> LENGTH: 1869
<212> TYPE: DNA
<213> ORGANISM: Trichoderma reesei

<400> SEQUENCE: 32
atgtttggtc ttgtccgccg actcggggtc ggcgcccttg tcgccgcagc cctttcctcc     60
ctcgctgccg ccgcgccagc caacgtcgcc atccgctccc tcgaggaacg ggctagcagc    120
gcagatagac ttgtgttttg ccactttatg attgggatat gtggtgatcg cacctccagt    180
accgattatg atgatgatat gcagcgagcc aaggccgcgg gcattgacgc cttttgccctt    240 aacattggtg tcgacggata cacgaccag cagctcaact ttgcctacga cgccgctgat    300
cgcgccggga tgaaggtgtt catctccttt gacttcaact ggtggagccc cggcaacgcg    360
gcaggcgtcg gccagaagat tgcccaatat gcgtcgcggc ccgcacagct ctacgtcgac    420
aaccgtccct ttgcatcgtc gtttgccggt gacggccttg acgtgaatac gctgcggaat    480
gcggccggca gcaacgtgta ctttgtgccc aacttccacc ccgggcagtc gtcgccgtcc    540
accatcgacg gggctctgaa ctggatggcc tgggacaaca acggcaacaa caaggccccc    600
aagcccggcc aaaacgtcac agtcgccgac ggcgacaact cctaccgcag ctggctcgcc    660
ggcaagccct acctcgcccc cgtctcgccc tggttcttca cccacttcgg cccagaggta    720
tcgtacagta agaactgggt cttccctggc ggctccctgt ggtacgaccg ctggcaggac    780
gtgctgcgcc agggcttcga gatggtcgaa atcgtcacct ggaacgatta cggtgagagc    840
cactacacgg ggcccctgga aagtcgacac tatgacgacg gaaactcgaa atggaccaac    900
gacatgccgc acgacggctt cctggacctg gcgaagcctt cattgccgc gtacaagaac    960 cgcgacacgg acgtggcgcc ctacatccag aatgagcagc tgatctactg gtatcggcgg   1020
aatctcaagg ggctggactg cgacgcgacc gacacgacgt cgaaccgccc ggcgaacaac   1080
ggcagcggca actacttcat gggtcggccc gacgggtggc agacgatgga cgacacggtg   1140
```

```
tatgtggtgg cgctgctcaa gagcgcgggc acggtgacgg tgacgtcggg cggcgccacg    1200
cagacgttcc agggcaccgc cggcgccaac ctgttcgagg tcccagccaa ccttgggcag    1260
cagaagtttg ccctgtcccg caacgggcag accgtcttca gcagcacgtc gctgatggat    1320
atcaccaatg tgtgcccgtg cggcatctac aacttcaacc cgtatgtcgg gactgtgccc    1380
gctggctttg acgacccgct cgggcccgat ggccttgctt cttttgacaat cggactgcac    1440 gtcacgactt gtcaggccaa gccgtcgctg ggaccaacc cgcccatcac ttccggcccc     1500
ggctcctcgg tgcccgtttc cactccgccc ggttccacga cccgcttctc gtcaacgccg    1560
gtttcatctc gctccagctc gtccacgccg ccggttagca cgccgccgcc tggccaagtc    1620
tgtgtcgccg gtacggtggc tgacggccag tccggcaact atattggcct ctgcaacttc    1680
agctgcaact tcgggtactg tccccccgga ccctgcaagt gcactgccta cggcgctccg    1740
atcaacccac cagcaacgaa tgggcgaaat gggtgcccct gcctggaga agacgatagt     1800 tatctgggcc tctgcagctt cagctgcaac cacaattact gtccgccaac agcatgccag    1860
tactgctga                                                            1869

<210> SEQ ID NO 33
<211> LENGTH: 2294
<212> TYPE: DNA
<213> ORGANISM: Trichoderma konilangbra

<400> SEQUENCE: 33
ggctccgcgg ccgcccccctt caccatgcta ggcattctcc gccgtctcgc gctcggcgcc      60
ctcgccgccg cggccctctc tcctctcgtc gtcgccgcgc ctgccaatgt cgccatccgc     120
tccctcgagg aacgggcgag tagcgcagac aggctcgtgt tctgccactt catggtacgt     180
gtggctgccc gaaaaggata cggcgtcatc ccgatagcaa cctgggctgt caccgcagca    240
cccgatgtta caaccactga cgtgccggcc tcgtttgtaga ttgggatatg cggtgatcgc    300
ggctccagca ctgattatga cgacgatatg caaagggcca aggcagcggg catcgacgcg    360
tttgcgttga acattggcgt cgatggatac acggaccagc agctcaactt tgcgtacgac    420
gccgccgacc gcgccgggat gaaggtgttc atctccttcg acttcaactg gtggagcccc    480
ggcaacgcag taggcgtcgg ccagaagatt gcccaatacg cgtcgcggcc cgcacagctc    540
tacgtcgaca accggccctt tgcgtcgtcg tttgccggcg atggccttga cgtgaatgcg    600
ctgcgcaacg ccgccggaag caacgtatac tttgtgccca acttccaccc cgggcagtcc    660
tccccgtcaa ccatcgacgg ggccctcaac tggatggtac gtttggacgt tgcgagtcaa    720
ggagaatccg cagaaaaagg ctgacagctg aggccaatgt gctcatgtgc tgacaygccg    780
gacaggcctg ggacaatgac ggaaacaaca aggcccccaa gccggccgc aacgtcaccg     840 tcgccgacgg cgacaactcg taccgtagct ggctgggcgg caagccctac ctggcccccg    900
tttcgccctg gttcttcacc cacttcggcc ccgaggtttc cttcagcaag aactgggtct    960
tcccgggcgg ctcgctcctc tacgaccgct ggcaggacgt gctgcrccag ggccccgaaa   1020
tggtcgagat catcacctgg aacgattacg gtgagagcca ctacaccggg cccctcaaaa   1080
gtcgccacta tgacgacgga aactcgaaat ggaccaacga catgccgcac gacggattcc   1140
tggacctgtc gaaaccgttt atagcggcgt acaagaaccg cgacacgaac gtggcacggt   1200
acgtccagtc cgaccagctc gtctactggt acagaaggac gctcaagggg ctggactgcg   1260
acgcgactga cacgacgtca aaccggcccg cgaacaacgc cagcggcaac tacttcatgg   1320
gccggcccga cgggtggcag acgatggacg acaccgtgta cgtggtggcg ctrctcacgg   1380
```

```
ccgcgggaac tgtgacggtg acgtccggcg gggccaccca gacgttccag ggcaccrccg    1440
gagccaacct gttcgaggtc ccggccaacc tgggccagca gaagtttgcc ctgtcccgca    1500
acgggcagac cgtcttcagc agcacatcgc tgatggatat cgctaatgtg tgcccgtgcg    1560
gcctctacaa cttcaacccg tatgtcggga ctgtcccgcc cggttttgac gacccgctgc    1620
aggctgatgg ccttgcgtcg ctgacgatcg gactgcacgt cacgacctgt caggccagac    1680
cctccctggg aacgaacccg cccatcactt ccggcccgg ctcctcggtg cccgcttcaa     1740
ccacccgctc gacttctccg cccggttcca cgagccgctt ctcgtcgacc ccggtttcgt    1800
cccgctccat ctcttcgacg ccaccggtca gcacgccgcc cctggccaa gtatgtgtgg     1860 ccggcacagt cgctgacggc cagtcgggca actatattgg cctatgcaac ttcagctgca    1920
agtaagtcgt cccacgttcc gtcatgatgt ctctgcctca gctaacatgt gccagcttcg    1980
gctactgtcc tcccgccct tgcaagtgca ccgccttgg cgctcccatc aacccaccgg      2040
cgaccaatgg gcgaaacgga tgcccttgc ctggagagga tgatagttac ttgggcctct     2100
gcagcttcag ttgcaaccat aactactgcc ctccgacggc atgccaatac tgctgaaagg    2160
gtgggcgcgc cgacccagct ttcttgtaca aagttggcat tataagaaag cattgcttat    2220
caatttgttg caacgaacag gtcactatca gtcaaaataa aatcattatt tgccatccag    2280
ctgatatccc ctat                                                      2294

<210> SEQ ID NO 34
<211> LENGTH: 1884
<212> TYPE: DNA
<213> ORGANISM: Trichoderma konilangbra

<400> SEQUENCE: 34
atgctaggca ttctccgccg tctcgcgctc ggcgccctcg ccgccgcggc cctctctcct    60
ctcgtcgtcg ccgcgcctgc caatgtcgcc atccgctccc tcgaggaacg ggcgagtagc    120
gcagacaggc tcgtgttctg ccacttcatg attgggatat gcggtgatcg cggctccagc    180
actgattatg acgacgatat gcaaagggcc aaggcagcgg catcgacgc gtttgcgttg     240 aacattggcg tcgatggata cacggaccag cagctcaact ttgcgtacga cgccgccgac    300
cgcgccggga tgaaggtgtt catctccttc gacttcaact ggtggagccc cggcaacgca    360
gtaggcgtcg gccagaagat tgcccaatac gcgtcgcggc ccgcacagct ctacgtcgac    420
aaccggccct ttgcgtcgtc gtttgccggc gatggcttg acgtgaatgc gctgcgcaac    480
gccgccggaa gcaacgtata ctttgtgccc aacttccacc ccgggcagtc ctccccgtca    540
accatcgacg gggccctcaa ctggatggcc tgggacaatg acggaaacaa caaggccccc    600
aagcccggcc gcaacgtcac cgtcgccgac ggcgacaact cgtaccgtag ctggctgggc    660
ggcaagccct acctggcccc cgtttcgccc tggttcttca cccacttcgg ccccgaggtt    720
tccttcagca agaactgggt cttccgggc ggctcgctcc tctacgaccg ctggcaggac    780
gtgctgcrcc agggccccga aatggtcgag atcatcacct ggaacgatta cggtgagagc    840
cactacaccg ggcccctcaa aagtcgccac tatgacgacg gaaactcgaa atggaccaac    900
gacatgccgc acgacggatt cctggacctg tcgaaaccgt ttatagcggc gtacaagaac    960
cgcgacacga acgtggcacg gtacgtccag tccgaccagc tcgtctactg gtacagaagg    1020
acgtccaagg ggctggactg cgagcgcact gacacgacgt caaaccggcc cgcgaacaac    1080
gccagcggca actacttcat gggccggccc gacgggtggc agacgatgga cgacaccgtg    1140
tacgtggtgg cgctrctcac ggccgcggga actgtgacgg tgacgtccgg cggggccacc    1200
```

```
cagacgttcc agggcaccrc cggagccaac ctgttcgagg tcccggccaa cctgggccag   1260
cagaagtttg ccctgtcccg caacgggcag accgtcttca gcagcacatc gctgatggat   1320
atcgctaatg tgtgcccgtg cggcctctac aacttcaacc cgtatgtcgg gactgtcccg   1380
cccggttttg acgacccgct gcaggctgat ggccttgcgt cgctgacgat cggactgcac   1440
gtcacgacct gtcaggccag accctccctg ggaacgaacc cgcccatcac ttccggcccc   1500
ggctcctcgg tgcccgcttc aaccacccgc tcgacttctc cgcccggttc cacgagccgc   1560
ttctcgtcga ccccgtttc gtcccgctcc atctcttcga cgccaccggt cagcacgccg    1620
ccccctggcc aagtatgtgt ggccggcaca gtcgctgacg gccagtcggg caactatatt   1680
ggcctatgca acttcagctg caacttcggc tactgtcctc ccggcccttg caagtgcacc   1740
gcctttggcg ctcccatcaa cccaccggcg accaatgggc gaaacggatg cccctttgcct  1800 ggagaggatg atagttactt gggcctctgc agcttcagtt gcaaccataa ctactgccct   1860
ccgacggcat gccaatactg ctga                                          1884
```

METHOD OF MAKING AND USING AN ALPHA-GLUCANASE COMPOSITION TO REDUCE OR REMOVE BIOFILM

PRIORITY

The present application is a 371 of PCT/US09/40013, filed on Apr. 9, 2009, which claims priority to U.S. Provisional Application Ser. No. 61/044,316, filed on Apr. 11, 2008, which is incorporated by reference in its entirety.

SEQUENCE LISTING

The sequence listing submitted via EFS, in compliance with 37 C.F.R. §1.52(e), is incorporated herein by reference. The sequence listing text file submitted via EFS contains the file "31149US_SequenceListing", created on May 25, 2011, which is 53,905 bytes in size.

BACKGROUND

The formation of dental plaque leads to dental caries, gingival inflammation, to periodontal disease, and eventually tooth loss. Dental plaque is a mixture of bacteria, epithelial cells, leukocytes, macrophages, and other oral exudate. The bacteria produce highly branched polysaccharides, which, together with micro-organisms from the oral cavity, form an adhesive matrix for the continued proliferation of dental plaque.

As dental plaque continues to accumulate, rock-hard white or yellowish deposits arise. These deposits are called calcified plaque, calculus, or tartar, and are formed in the saliva from plaque and minerals, e.g., calcium.

There is an ongoing need for new ways to prevent and/or reduce dental plaque and associated tooth decay.

SUMMARY

In one aspect, an isolated α-glucanase is provided, comprising an amino acid sequence that is (a) at least 99% identical to the mature *Hypocrea tawa* α-glucanase (amino acid residues 38-635 of SEQ ID NO: 1); or (b) at least 85% identical to the mature *Trichoderma konilangbra* α-glucanase (amino acid residues 38-627 of SEQ ID NO: 3).

In another aspect, an isolated polynucleotide encoding a subject α-glucanase, and recombinant nucleic acid containing the isolated polynucleotide is provided. A vector and a host cell containing the recombinant nucleic acid are also provided.

In another aspect, a cell culture is provided. In some embodiments, the cell culture contains a growth medium and a population of the above-described host cells. The cell culture may be used to produce a subject α-glucanase by maintaining the cell culture under conditions suitable for production of the isolated α-glucanase. If the α-glucanase is secreted, it may be harvested from the growth medium.

In another aspect, a method of producing protein is provided, comprising maintaining the culture of cells described above under conditions suitable for production of the isolated α-glucanase. In some embodiments, the method further comprises harvesting the α-glucanase from the growth medium.

In another aspect, a method is provided, comprising receiving an isolated α-glucanase selected from the following: (a) α-glucanase having an amino acid sequence that is at least 99% identical to that of mature *Hypocrea tawa* α-glucanase (amino acid residues 38-635 of SEQ ID NO: 1); (b) α-glucanase having an amino acid sequence that is at least 85% identical to that of mature *Trichoderma reesei* α-glucanase (amino acid to residues 38-622 of SEQ ID NO: 2); or (c) α-glucanase having an amino acid sequence that is at least 85% identical to that of mature *Trichoderma konilangbra* α-glucanase (amino acid residues 38-627 of SEQ ID NO: 3); and admixing the isolated α-glucanase with an orally acceptable excipient to make an oral care composition. In some embodiments, the α-glucanase is not identical to *Trichoderma reesei* α-glucanase (amino acid residues 38-622 of SEQ ID NO: 2). In some embodiments, the method further comprises packaging the oral care composition.

In another aspect, an oral care composition is provided, comprising (a) an orally acceptable excipient; and (b) an isolated α-glucanase.

In a related aspect, an oral care composition is provided, comprising: an orally acceptable excipient and an isolated α-glucanase selected from the following: (a) α-glucanase having an amino acid sequence that is at least 99% identical to that of mature *Hypocrea tawa* α-glucanase (amino acid residues 38-635 of SEQ ID NO: 1); (b) α-glucanase having an amino acid sequence that is at least 85% identical to that of mature *Trichoderma reesei* α-glucanase (amino acid residues 38-622 of SEQ ID NO: 2); or (c) α-glucanase having an amino acid sequence that is at least 85% identical to that of mature *Trichoderma konilangbra* α-glucanase (amino acid residues 38-627 of SEQ ID NO: 3). In some embodiments, the α-glucanase is not identical to *Trichoderma reesei* α-glucanase (amino acid residues 38-622 of SEQ ID NO: 2).

In some embodiments, the α-glucanase is present in the composition at a concentration of 0.0001% to 5% by weight of the composition.

In some embodiments, the oral care composition further comprises a second enzyme. In particular embodiments, the second enzyme is a deaminase, esterase, glycosidase, lipase, oxidase, peroxidase, protease, urease or cellulase.

In some embodiments, the composition is formulated as a toothpaste, although other oral care formulations are envisioned. In some embodiments, the composition comprises at least one of a thickener, a surfactant, a humectant, and an abrasive, for example.

In another aspect, a method is provided, in which the isolated α-glucanase is received, and then admixing with an orally acceptable excipient to make an oral care to composition is provided. The oral care composition may be packaged.

In yet another aspect, a method comprising contacting a subject oral care composition with a tooth under conditions suitable for activity of the α-glucanase is provided. The contacting may be performed using, e.g., a toothbrush. In particular cases, the method results in prevention and/or reduction in dental plaque.

BRIEF DESCRIPTION OF THE DRAWINGS

FIG. 1 shows an amino acid sequence alignment of α-glucanases from *Hypocrea tawa* (SEQ ID NO: 1), *Trichoderma reesei* (SEQ ID NO: 2); *Trichoderma konilangbra* (SEQ ID NO: 3) and *T. harzianum* (SEQ ID NO: 4), and a consensus sequence (SEQ ID NO: 5) based on the alignment. Various features of the α-glucanases are indicated, such as the signal sequence, the catalytic domain, the linker domain, and the glucan-binding domain.

DEFINITIONS

Figures 2, 3:
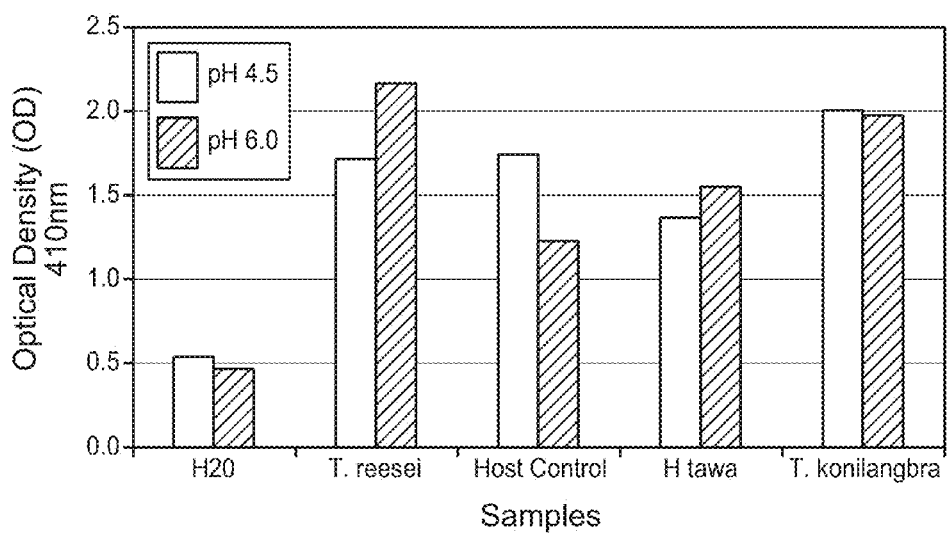
FIG. 2 is a table that summarizes the results of HPLC analysis of the insoluble glucan hydrolysates obtained following overnight incubation with various cell-free culture solutions.
FIG. 3 shows the activity of supernatants from cultures of *T. reesei* expressing the putative alpha-1,3-glucanases from *T.* reesei, H. tawa, and T. konilangbra at pH 4.5 and at pH 6.0. The native alpha-glucanases were not deleted from the host strain. The glucan hydrolysis reactions were loaded based on culture volume, not protein content.

Unless defined otherwise herein, all technical and scientific terms should be given their ordinary meaning as used in the art. The following terms are defined for clarity. Other definitions may appear elsewhere in the specification.

As used herein, the term "α-glucanase" refers to an enzyme that hydrolyses 1,3-α-D-glucosidic linkages in a polysaccharide. The α-glucanases s described herein have an activity described as EC 3.2.1.59, according to IUBMB enzyme nomenclature, and can hydrolyse insoluble glucan. The systematic name for an α-glucanase is 1,3(1,3;1,4)-α-D-glucan 3-glucanohydrolase. This enzyme may be referred to as 1,3-α-glucanase in certain to publications. Note that the present enzymes may have other activities in addition to 1,3-α-D-glucosidic activity, including but not limited to 1,2-α-D-glucosidic activity.

As used herein, the term "oral care composition" refers to an admixture of ingredients, which in the ordinary course of usage is not intentionally swallowed for purposes of systemic administration of particular therapeutic agents, but is rather retained in the oral cavity for a time sufficient to contact dental surfaces and/or oral tissues for purposes of delivering a beneficial agent to the oral activity. An oral composition may be in the form of toothpaste, dentifrice, tooth powder, tooth gel, subgingival gel, mouthrinse, denture product, mouthspray, lozenge, oral tablet, chewing gum, or the like. The oral composition may also be incorporated onto strips or films for direct application or attachment to oral surfaces.

Unless otherwise specified, the term "dentifrice" refers to paste, gel, solid or liquid oral care composition formulation. Examples of dentifrices are toothpaste, tooth gel, and tooth powder. A dentifrice may be a single phase composition or may be a combination of two or more separate compositions. A dentifrice may be in any desired form, such as deep striped, surface striped, multilayered, having the gel surrounding the paste, or any combination thereof. Each composition in a dentifrice comprising two or more separate compositions may be contained in a physically separated compartment of a dispenser and dispensed side-by-side.

As used herein, the term "orally acceptable carrier" refers to a safe and effective material for use in an oral care composition. Such materials include fluoride ion sources, anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

As used herein, the terms "tooth" or "teeth" refers to natural teeth as well as artificial teeth or dental prosthesis.

As used herein, the term "enamel" refers to the part of a tooth that is normally visible and is composed of mostly minerals, including hydroxylapatite. Enamel encompasses naturally-occurring enamels in teeth of humans and animals as well as enamel-like substance used to replace damaged or missing teeth parts, including resins and porcelains used for such purposes.

As used herein, the terms "tartar" and "calculus" are used interchangeably to refer to mineralized dental plaque deposits.

As used herein, the term "glycocalyx" refers to extracellular polymeric material produced by some bacteria, epithelial cells, and other cells, which forms a coating on the surface of teeth and serves as a matrix for the attachment of plaque.

As used herein, the term "plaque" refers to a biofilm that forms on the surface of a tooth (or of teeth). The microorganisms that form the biofilm are mostly bacteria, including but not limited to *Streptococcus mutans, Streptococcus anaerobes, Fusobacterium* spp., and *Actinobacteria* spp. Plaque may form on, be supported by, or be part of a glycocalyx.

The microorganisms present in dental plaque are all naturally present in the oral cavity, and are normally harmless. However, failure to remove plaque by regular tooth brushing means that they are allowed to build up in a thick layer. Those microorganisms nearest the tooth surface convert to anaerobic respiration; it is in this state that they start to produce acids.

As used herein, the term "recombinant" refers to a polynucleotide or polypeptide that does not occur in, is not secreted by, or has an altered expression pattern in, a wild type host cell. Recombinant polypeptides and polynucleotides have respective sequences that are different from the wild-type sequence, have different temporal or spatial expression patterns from wild type polypeptides and polynucleotides, and/or are expressed at different levels than wild type polypeptides and polynucleotides. A recombinant molecule may contain two or more naturally-occurring sequences that are linked together in a way that does not occur naturally. A recombinant cell contains a recombinant polynucleotide or a recombinant polypeptide.

As used herein, the term "heterologous" refers to elements that are not normally associated with each other. For example, if a host cell produces a heterologous protein, that protein is not normally produced in that host cell. Likewise, a promoter that is operably linked to a heterologous coding sequence is a promoter that is operably linked to a coding sequence that it is not usually operably linked to in a wild-type host cell. The term "homologous", with reference to a polynucleotide or protein, refers to a polynucleotide or protein that occurs naturally in a host cell.

As used herein, the terms "protein" and "polypeptide" are used interchangeably to refer to a chain of amino acids linked by peptide bonds. Unless otherwise specified polypeptides are written in the standard N-terminal to C-terminal direction.

As used herein, a "signal sequence" is a sequence of amino acids present at the N-terminal portion of a protein which facilitates the secretion of the mature form of the protein from the cell. The definition of a signal sequence is a functional one, although the structures of many signal sequence are known. The mature form of the extracellular protein lacks the signal sequence, which is cleaved off during the secretion process.

As used herein, a "coding sequence" is a DNA segment that encodes a polypeptide.

As used herein, the term "nucleic acid" encompasses DNA, RNA, hybrids, and synthetic or chemically-modified nucleic acids, whether single-stranded or double-stranded. The terms "nucleic acid" and "polynucleotide" are used interchangeably to refer to a chain of nucleosides linked by phosphodiester, sulfodiester, or similar bonds. Unless otherwise specified polynucleotides are written in the standard 5' to 3' direction.

As used herein, a "vector" refers to a polynucleotide designed to introduce nucleic acids into one or more host cells. Vectors can autonomously replicate in different host cells and include: cloning vectors, expression vectors, shuttle vectors, plasmids, phage particles, cassettes and the like.

As used herein, an "expression vector" refers to a DNA construct comprising a protein-coding region that is operably linked to a suitable control sequence capable of effecting expression of the protein in a suitable host cell. Such control sequences may include a promoter to effect transcription, an optional operator sequence to control transcription to produce mRNA, a sequence encoding suitable ribosome binding sites on the mRNA, and enhancers and other sequences which control the termination of transcription and translation.

As used herein, a "promoter" is a regulatory sequence that initiates transcription of a downstream nucleic acid.

As used herein, the term "operably linked" refers to an arrangement of elements that allows the elements to function in a described or apparent manner. For example, a promoter is operably linked to a coding sequence if it controls the transcription of the sequence.

As used herein, the term "selective/selectable marker" refers to a protein capable of to expression in a host that allows for ease of selection of those cells containing an introduced nucleic acid or vector. Examples of selectable markers include, but are not limited to, proteins that confer resistance to antimicrobials (e.g., hygromycin, bleomycin, or chloramphenicol) and/or genes that confer a metabolic advantage, such as a nutritional advantage on the host cell.

As used herein, the term "derived from" encompasses the terms "originated from," "obtained" or "obtainable from," and "isolated from".

As used herein, a "non-pathogenic" organism is an organism that is not pathogenic (i.e., disease or disorder-causing) to humans.

As used herein, the terms "recovered," "isolated," and "separated" refer to a protein, cell, nucleic acid or amino acid that is removed from at least one component with which it is naturally associated.

As used herein, the terms "transformed," "stably transformed," and "transgenic," used in reference to a cell, means that the cell has a non-native (e.g., heterologous) nucleic acid sequence integrated into its genome or as an episomal plasmid that is maintained over multiple generations.

As used herein, the term "expression" refers to the process by which a polypeptide is produced based on the nucleic acid sequence of a gene. The process includes both transcription and translation.

As used herein, the term "introduced" in the context of inserting a nucleic acid sequence into a cell, means "transfection," or "transformation," or "transduction," and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the term "compatible" means that the components of a specified composition are capable of being comingled (admixed) without interaction in a manner which would substantially reduce the stability and/or efficacy of a component in the composition.

As used herein, the term "lozenge" includes but is not limited to: breath mints, troches, pastilles, microcapsules, and fast-dissolving solid forms including freeze dried forms (cakes, wafers, thin films, tablets) and compressed tablets.

As used herein, the term "fast-dissolving solid form" means that a solid dosage form dissolves in less than about 60 seconds, less than about 15 seconds, or less than about 5 seconds, after placing the solid dosage form in the oral cavity or a container containing dental prosthetics.

Numeric ranges are inclusive of the numbers defining the range. All percentages and ratios used herein are by weight of the specific oral composition and not of the overall oral formulation that is delivered, unless otherwise specified. The singular articles "a," an," and the," include the plural unless otherwise specified or apparent from context.

Headings are provided for ease of reading and should not be construed as limitations. The description included under one heading generally applies to the document as a whole, unless otherwise specified or apparent from context.

Exemplary material and methods are described, although other methods and materials may result in similar or equivalent results. All patents and publications, including all sequences disclosed within such patents and publications, are expressly incorporated by reference.

DETAILED DESCRIPTION

Described are compositions and methods relating to polypeptides having α-glucanase activity. The compositions and methods are useful for reducing or preventing the formation of plaque, and for reducing or preventing the underlying physiological conditions that promote the formation of plaque.

A. Polypeptides, Polynucleotides, and Host Cells

One aspect of the present compositions and methods relates to an isolated α-glucanase. In some embodiments, the α-glucanase comprises an amino acid sequence that is at least 98% identical to (e.g., at least 99% or 99.5% identical to) the amino acid sequence of the mature *Hypocrea tawa* α-glucanase (amino acid residues 38-635 of SEQ ID NO: 1). In particular embodiments, the α-glucanase comprises the amino acid sequence of the mature *H. tawa* α-glucanase (amino acid residues 38-635 of SEQ ID NO: 1).

In some embodiments, the α-glucanase comprises an amino acid sequence that is at least 85% identical to (e.g., at least 90%, 91%, 92%, 93%, 94%, 95%, 96%, 97%, 98%, or 99% identical to) the amino acid sequence of the mature *Trichoderma konilangbra* α-glucanase (amino acids 38-627 of SEQ ID NO: 3). In particular embodiments, the α-glucanase comprises the amino acid sequence of the mature *T. konilangbra* α-glucanase (amino acids 38-627 of SEQ ID NO: 3).

In some embodiments, the α-glucanase comprises an amino acid sequence that is at least 85% identical to (e.g., at least 90%, 91%, 92%, 93%, 94%, 95%, 96%, 97%, 98%, or 99% identical to) the amino acid sequence of the mature *Trichoderma reesei* α-glucanase (amino acids 38-622 of SEQ ID NO: 2). In particular embodiments, the α-glucanase comprises an amino acid sequence that is not identical to the amino acid sequence of the mature *T. reesei* α-glucanase (amino acids 38-622 of SEQ ID NO: 2).

In some embodiments, the α-glucanase is similar to but not identical to a wild type α-glucanase. For example, in some embodiments, the α-glucanase has an amino acid sequence that is at least 98% identical to, but not identical to, the mature *H. tawa* α-glucanase (amino acid residues 38-635 of SEQ ID NO: 1). Likewise, in certain embodiments, the α-glucanase may have an amino acid sequence that at least 85% identical to, but not identical to, the mature *T. reesei* or *T. konilangbra* α-glucanase (amino acids 38-622 of SEQ ID NO: 2 or amino acids 38-627 of SEQ ID NO: 3, respectively).

The amino acid sequences for over 50 different α-glucanases are known and have been deposited in NCBI's Genbank database, including those from *Aspergillus niger* (accession no.: XP_001390909.1; GID: 145236523), *Penicillium purpurogenum* (accession no.: AAF27912.1; GID: 6752866), *Emericella nidulans* (accession no.: CAC48025.1; GID: 15072711) and *Cryptococcus neoformans* (accession no.: AAW47079.1; GID: 57230770). These Genbank accessions are incorporated by reference in their entirety, including the nucleic acid and protein sequences therein and the annotation of those sequences, as of the earliest filing date of this patent application. An entry describing a domain that is conserved in α-glucanases has been deposited as pfam03659 in NCBI's Conserved Domain Database (Marchler-Bauer et al. CDD: a conserved domain database for interactive domain family analysis. (2007) *Nucleic Acids Res.* 35:D237-40). The sequence of a α-glucanase from *S. pombe*, as well as a discussion of the structure of α-glucanases is found in Fuglsang et al. ((2000) *J. Biol. Chem.* 275:2009-18).

Figure 1:
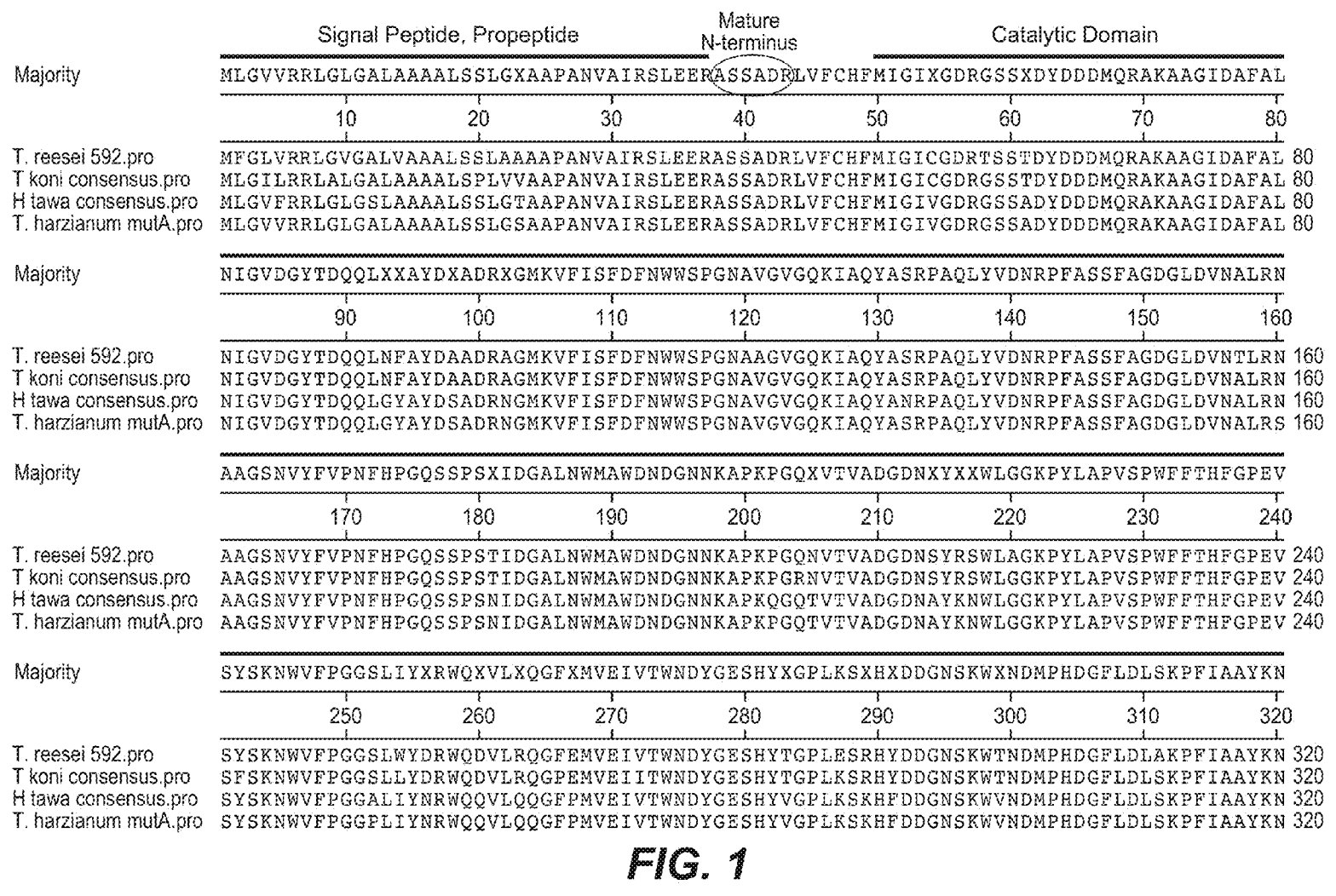

Guidance for which amino acids can be changed to produce an active variant of the to wild-type α-glucanases of *H. tawa*, *T. reesei* and *T. konilangbra* that retains α-glucanase activity can be obtained, for example, by aligning the amino acid sequences of those α-glucanase proteins, identifying amino acids that are at identical positions in the proteins but are different between the proteins, and transferring those amino acids from one protein to the other. Exemplary sequence alignments are shown in FIG. 1, and in Fuglsang et al. (supra).

A variant polypeptide may include conservative amino acid substitutions that preserve the general charge, hydrophobicity/hydrophilicity, and/or steric bulk of the amino acid being substituted, while imparting other beneficial biochemical properties on the polypeptide. Non-limiting examples of conservative substitutions include those between the following groups: Gly/Ala, Val/Ile/Leu, Lys/Arg, Asn/Gln, Glu/Asp, Ser/Cys/Thr and Phe/Trp/Tyr. These and other conservative substitutions are shown in the Table, below.

| Original Amino Acid | Code | Conservative Substitution |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3, 4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Alternatively, the amino acid substitutions are not conservative and change the general charge, hydrophobicity/hydrophilicity, and/or steric bulk of the amino acid being substituted.

Assays for evaluating α-glucanase activity are described in a variety of publications, including: Fuglsang et al. (supra), Inoue et al. ((1988) *Carbohydr. Res.* 182:277-86), Ait-Lahsen et al. ((2001) *Appl. Environ. Microbiol.* 67:5833-9), and Sumitomo et al. ((2007) *Biochim. Biophys. Acta.* 1770:716-24).

Also provided is an isolated polynucleotide encoding an α-glucanas as described, to and a recombinant nucleic acid containing the isolated polynucleotide. Given that the genetic code is known, such a polynucleotide can be readily designed based on the amino acid sequence. In one embodiment, the isolated polynucleotide has a nucleotide sequence that is at least 70% identical to (e.g., at least 80% identical to, at least 90% identical to, at least 95% identical to, at least 98% identical to), or may hybridize under stringent conditions to, the nucleotide sequence of a wild type *H. tawa* α-glucanase gene or coding sequence (e.g., SEQ ID NOs: 29 and 30, respectively), a wild type *T. reesei* α-glucanase gene or coding sequence (e.g., SEQ ID NOs: 31 and 32, respectively), or a wild type *T. konilangbra* α-glucanase gene or coding sequence (e.g., SEQ ID NOs: 33 and 34, respectively). In certain embodiments, the coding sequence of the α-glucanase is codon optimized for expression of the α-glucanase in the host cell used. Since codon usage tables listing the usage of each codon in many host cells, including *Trichoderma reesei* and various other yeast and bacterial host cells are known in the art (see, e.g., Nakamura et al. (2000) *Nucl. Acids Res.* 28:292) or readily derivable, such nucleic acids can be readily designed given the amino acid sequence of a α-glucanase to be expressed.

An expression vector and a host cell containing the recombinant nucleic acid are also provided. In certain embodiments, the host cell is bacterial (e.g., a *Bacillus* sp. or *Streptomyces* sp. host cell) or filamentous fungal host cell that, in certain cases, may be non-pathogenic, i.e., non-pathogenic to humans. In particular embodiments, the cells may be filamentous fungal cells of a strain that has a history of use for production of proteins that has GRAS status, i.e., a Generally Recognized as Safe, by the United States Food and Drug Administration (FDA).

In particular embodiments, the subject fungal cell may be a cell of the following species: *Trichoderma*, (e.g., *Trichoderma reesei* (previously classified as *T. longibrachiatum* and currently also known as *Hypocrea jecorina*), *Trichoderma viride*, *Trichoderma koningii*, and *Trichoderma harzianum*)); *Penicillium* spp., *Humicola* spp. (e.g., *Humicola insolens* and *Humicola grisea*); *Chrysosporium* spp. (e.g., *C. lucknowense*), *Gliocladium* spp., *Aspergillus* spp. (e.g., *Aspergillus oryzae*, *Aspergillus niger*, *Aspergillus nidulans*, *Aspergillus kawachi*, *Aspergillus aculeatus*, *Aspergillus japonicus*, *Aspergillus sojae*, and *Aspergillus awamori*), *Fusarium* spp., *Neurospora* spp., *Hypocrea* spp., or *Emericella* spp. (see, also, Innis et al. (1985) *Science* 228:21-26), among others. In some embodiments, subject fungal cells may be strains of *Aspergillus niger* which include American Type Culture Collection (ATCC®; Manassas, Va., USA) 22342, ATCC® 44733, ATCC® 14331 and strains derived therefrom. In some embodiments, a host cell may be one wherein native genes have been deleted or inactivated. For example, genes corresponding to protease genes or genes corresponding to cellulase genes may be deleted or inactivated.

The above described nucleic acid may be present in the nuclear genome of the host cell or may be present in a plasmid that replicates in the host cell, for example, a transient expression vector, a shuttle vector, an artificial chromosome, and the like.

In particular embodiments, the α-glucanase may be produced by expressing a fusion protein containing a signal sequence operably linked to the α-glucanase in a fungal host cell. In such embodiments, the α-glucanase may be secreted into culture medium, where it can be harvested. The signal sequence of the fusion protein may be any signal sequence that facilitates protein secretion from the host cell. The signal sequence employed may be endogenous or non-endogenous to the host cell and, in certain embodiments, may be a signal sequence of a protein that is known to be highly secreted from a *Trichoderma* sp. or *Aspergillus* sp. host cell. Such signal sequence include, but are not limited to: the signal sequence of cellobiohydrolase I, cellobiohydrolase II, endoglucanases I, endoglucanases II, endoglucanases III, α-amylase, aspartyl proteases, glucoamylase, mannanase, glycosidase and barley endopeptidase B (see, e.g., Saarelainen (1997) *Appl. Environ. Microbiol.* 63:4938-40). In a particular embodiment, an α-glucanase may be secreted using its own (i.e., the endogenous) signal sequence.

It follows that in some embodiments an α-glucanase is produced by introducing a nucleic acid into a host cell, which nucleic acid comprises a signal sequence-encoding portion operably linked to a α-glucanase-encoding portion, where translation of the nucleic acid produces a fusion protein comprising an α-glucanase portion having an N-terminal signal sequence for secretion of the α-glucanase portion from the host cell.

In particular embodiments, the fusion protein may further contain, in addition to a signal sequence, a carrier protein that is a portion of a protein that is endogenous to and highly secreted by the host cell. Suitable carrier proteins include those of *T. reesei* mannanase I (Man5A, or MANI), *T. reesei* cellobiohydrolase II (Ce16A, or CBHII) (see, e.g., Paloheimo et al. (2003) *Appl. Environ. Microbiol.* 69:7073-82), or *T. reesei* cellobiohydrolase I (CBHI). In one embodiment, the carrier protein is a truncated *T. reesei* CBH1 protein that includes the CBH1 core region and part of the CBH1 linker region. A nucleic acid encoding a fusion protein containing, from amino-terminus to carboxy-terminus, a signal sequence, a carrier protein and a subject α-glucanase in operable linkage may therefore be employed.

In addition to a coding sequence, the nucleic acid may further contain other elements that are necessary for expression of the α-glucanase in the host cell. For example, the nucleic acid may contain a promoter for transcription of the coding sequence, and a transcriptional terminator. Exemplary promoters that may be employed in *T. reesei* include the *T. reesei* cbh1, cbh2, eg11, eg12, eg5, xln1 and xln2 promoters, or a hybrid or truncated version thereof. For example, the promoter may be a *T. reesei* cbh1 promoter.

Suitable terminators include the *T. reesei* cbh1, cbh2, eg11, eg12, eg5, xln1 and xln2 terminators, and many others, including, for example, the terminators from *A. niger* or *A. awamori* glucoamylase genes (Nunberg et al. (1984) *Mol Cell Biol.* 4:2306-15); Boel et al. (1984) *EMBO J.* 3:1097-102; and Boel et al. (1984) *EMBO J.* 3:1581-85), *Aspergillus nidulans* anthranilate synthase genes, *Aspergillus oryzae* TAKA amylase genes, or *A. nidulans* trpC (Punt et al. (1987) *Gene* 56:117-24). The promoter and/or terminator may be native or non-endogenous to the *Trichoderma* sp. host cell.

A culture of host cells (i.e., a composition containing a population of host cells and growth media) is also provided. The growth medium of the culture may contain the α-glucanase described above. In certain embodiments, the cell culture may contain growth medium and a population of the above-described cells. The cell culture may be used to produce a subject α-glucanase by maintaining the cell culture under conditions suitable for production of the isolated α-glucanase. If the α-glucanase is secreted, it may be harvested from the growth medium.

Methods of expressing proteins in filamentous fungi, including methods in which cells are engineered to produce secreted protein include those described in U.S. Pat. Nos. 6,022,725 and 6,268,328, and in published U.S. Pat. App. Nos. 20060041113, 20060040353, 20060040353, and 20050208623, which are incorporated herein by reference. In addition, general methods for the transformation of *Aspergillus* strains are disclosed in Cao et al. (2000) *Protein Sci.* 9:991-1001) and Yelton et al. (1984) *Proc. Natl. Acad. Sci. USA* 81:1470-74) and general methods for the transformation of *Trichoderma* strains are disclosed in Nevalainen et al. (1992) "The Molecular Biology of *Trichoderma* and its Application to the Expression of Both Homologous and Heterologous Genes" in Molecular Industrial Mycology, Eds. Leong and Berka, Marcel Dekker Inc., NY, pp 129-48).

If it is secreted in to culture medium, the α-glucanase may be recovered by any convenient method, e.g., by precipitation, centrifugation, affinity, filtration or any other method known in the art. For example, affinity chromatography (Tilbeurgh et al. (1984) *FEBS Lett.* 16:215); ion-exchange chromatographic methods (Goyal et al. (1991) *Biores. Technol.* 36:37; Fliess et al. (1983) *Eur. J. Appl. Microbiol. Biotechnol.* 17:314; Bhikhabhai et al. (1984) *J. Appl. Biochem.* 6:336; and Ellouz et al. (1987) *Chromatography* 396:307), including ion-exchange using materials with high resolution power (Medve et al. (1998) *J. Chromatography A.* 808153; hydrophobic interaction chromatography (Tomaz and Queiroz (1999) *J. Chromatography A.* 865:123; two-phase partitioning (Brumbauer et al. (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; or gel filtration using, e.g., Sephadex G-75, may be employed. In particular embodiments, the α-glucanase may be used without purification from the other components of the culture medium. In these embodiments, the culture medium may simply be concentrated, for example, and then used without further purification of the protein from the components of the growth medium, or used without any further modification.

B. Oral Care Compositions

An aspect of the present compositions and methods relates to an oral care composition. The oral care composition contains one or more of the described α-glucanases and an orally acceptable carrier. Each of the one or more α-glucanases may be present in the composition at a concentration in the range of 0.0001% to 5% (e.g., 0.0001% to 0.0005%, 0.0005% to 0.001%, 0.001% to 0.005%, 0.005% to 0.01%, 0.01% to 0.05%, 0.05% to 0.1%, 0.1% to 0.5%, 0.5% to 1%, or 1% to 5%) by weight, although concentrations outside of this range are envisioned. The oral care composition may be made by a method that includes admixing the α-glucanase with an orally acceptable excipient. In certain cases, this method may further include packing the oral care composition.

The oral care composition may be in the form of, e.g., a dentifrice, toothpaste, tooth powder, topical oral gel, mouthrinse, denture product, mouthspray, lozenge, oral tablet, or chewing gum. The oral composition may also be incorporated onto strips, films, floss, or tape for direct application or attachment to oral surfaces.

An orally acceptable carrier may comprise one or more compatible solid or liquid filler diluents or encapsulating substances, which are suitable for topical oral administration. Suitable carriers or excipients include the usual and conventional components of dentifrices (including non-abrasive gels and gels for subgingival application), mouth rinses, mouth sprays, chewing gums, and lozenges (including breath mints) as more fully described hereinafter. The present oral care compositions in aqueous form may optimally have a pH ranging from about 4.0 to about 10.0, e.g., from about 5.0 to about 8.0.

In some embodiments, the carrier is selected based on the manner in which the way the composition is to be introduced into the oral cavity. For example, if a toothpaste (including tooth gels, etc.) is to be used, then a "toothpaste carrier" may be chosen (comprising e.g., abrasive materials, surfactants, binders, humectants, flavoring and sweetening agents, etc.) as disclosed in e.g., U.S. Pat. No. 3,988,433, to Benedict. If a mouthrinse is to be used, then a "mouthrinse carrier" may be chosen (comprising e.g., water, flavoring and sweetening agents, etc.), as disclosed in e.g., U.S. Pat. No. 3,988,433 to Benedict. If a mouth spray is to be used, then a "mouth spray carrier" may be chosen or if a lozenge is to be used, then a "lozenge carrier" may be chosen (e.g., a candy base). If a chewing gum is to be used, a "chewing gum carrier" may be chosen (comprising e.g., gum base, flavoring and sweetening agents). If a sachet is to be used, then a "sachet carrier" may be chosen (e.g., sachet bag, flavoring and sweetening agents). If a subgingival gel is to be used (for delivery of actives into the periodontal pockets or around the periodontal pockets), then a "subgingival gel carrier" may be chosen. Other useful carriers suitable for the preparation of compositions of the present invention are well known in the art. Their selection may depend on secondary considerations like taste, cost, shelf stability, the desire for a sugar or salt-free composition, and the like.

In some embodiments, the composition may be in the form of a non-abrasive gel, e.g., a subgingival gel, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. In certain cases, the composition may comprise an anticaries agent (from about 0.05% to about 0.3% as fluoride ion), and an anticalculus agent (from about 0.1% to about 13%).

In other embodiments, the composition may also be in the form of a dentifrice, such as a toothpaste, tooth gel or tooth powder. Components of such toothpaste and tooth gels may include one or more of a dental abrasive (from about 5% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powder may contain substantially all non-liquid components.

One exemplary dentifrice composition is described in U.S. Pat. No. 6,238,648, and has the following formulation (w/w):

| | |
|---|---|
| Glycerin | 14.0 |
| Polyethylene Glycol 300 | 4.5 |
| Silica | 21.5 |
| Tetrasodium Pyrophosphate | 4.5 |
| Water | 23.5 |
| Xanthan Gum | 0.3 |
| Carboxymethyl Cellulose | 0.5 |
| Sodium Fluoride | 0.2 |
| Flavor | 1.0 |
| Sodium Lauryl Sulfate (27.9% Solution) | 4.5 |
| Sodium Saccharin | 0.4 |
| Titanium Dioxide | 0.4 |

-continued

| | |
|---|---|
| Sodium Bicarbonate | 0.9 |
| Sodium Carbonate, Anhydrous | 1.4 |
| Poloxamer 407 | 1.8 |
| Xylitol | 10.0 |
| Propylene Glycol | 10.6 |
| TOTAL | 100.00 |

Another exemplary dentifrice composition is described in U.S. Pat. No. 5,578,295, and has the following formulation (w/w):

| | |
|---|---|
| Triclosan diphosphate | 1 |
| Sorbitol | 33 |
| Saccharin | 0.46 |
| Silica | 22 |
| NaF | 0.243 |
| Glycerin | 9 |
| NaOH (50%) | 0.2 |
| Carbopol | 0.2 |
| Keltrol | 0.6 |
| TiO.sub.2 | 0.5 |
| Sodium alkyl sulphate (28% soln.) | 4 |
| PEG | 6 |
| 3 FD&C Blue #1 (1% soln) | 0.05 |
| Flavor | 1.1 |
| Water | q.s. |

In some embodiments, the composition is a mouthwash, including mouth spray. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

In certain embodiments, the composition may be dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

Lozenges may include discoid-shaped solids comprising a therapeutic agent in a flavored base. The base may be a hard sugar candy, glycerinated gelatin or combination of sugar with sufficient mucilage to give it form. These dosage forms are generally well known in the art.

In another embodiment, the invention provides a dental implement impregnated with the composition provided herein. The dental implement may comprise an implement for contact with teeth and other tissues in the oral cavity, the implement being impregnated with a composition comprising an oxidase with polyethyleneimine or sorbitol. The dental implement may be in the form of impregnated fibers including dental floss or tape, chips, strips, films, toothpicks, and polymer fibers.

Exemplary materials that may be present in an orally acceptable carrier are described below.

Abrasives

Dental abrasives include many different materials. The material selected may be compatible within the composition of interest and may not excessively abrade dentin. Suitable abrasives may include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

One class of abrasives for use in the compositions is a particulate thermo-setting polymerized resin. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types may be selected because of their benefits dental cleaning and polishing performance without unduly abrading tooth enamel or dentine. The silica abrasive polishing materials, as well as other abrasives, may have an average particle size ranging between about 0.1 to about 30 microns, or from about 1 to about 15 microns. The abrasive can be precipitated silica or silica gels such as the silica xerogels.

Mixtures of abrasives may also be used. The total amount of abrasive in dentifrice compositions may range from about 6% to about 70% by weight. Toothpastes may contain from about 10% to about 50% of abrasives, by weight of the composition. Solution, mouth spray, mouthwash and non-abrasive gel compositions may contain no abrasive.

Surfactants

The present compositions may also contain a surfactant, e.g., a sarcosinate surfactant, isethionate surfactant or taurate surfactant. In certain embodiments, the composition may contain alkali metal or ammonium salts of these surfactants. In certain cases, the composition may contain sodium and potassium salts of the following: lauroyl sarcosinate, myristoyl sarcosinate, palmitoyl sarcosinate, stearoyl sarcosinate and oleoyl sarcosinate. Other suitable compatible surfactants may be used in place of or in combination with these surfactants.

Suitable anionic surfactants include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants may also be utilized.

Suitable cationic surfactants include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. In certain cases, surfactant compounds may be the quaternary ammonium fluorides with detergent properties. Some cationic surfactants may act as germicides in the composition.

Suitable nonionic surfactants include compounds produced by the condensation of alkylene oxide groups (hydrophilic in nature) with an organic hydrophobic compound which may be aliphatic or alkylaromatic in nature. Examples include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Suitable zwitterionic synthetic surfactants include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. Amidobetaines are exemplified by cocoamidoethyl betaine, cocoamidopropyl betaine, lauramidopropyl betaine and the like. In certain embodiments, the betaines in the composition are cocoamidopropyl betaine or lauramidopropyl betaine.

Surfactants may be present at a concentration in the range of about 0.1% to about 2.5%, from about 0.3% to about 2.5%, or from about 0.5% to about 2.0% by weight of the total composition.

Anti-Plaque Agent

The compositions may also include an anti-plaque agent, such as a synthetic anionic polymer, e.g., polyacrylate or copolymers of maleic anhydride or acid and methyl vinyl to ether as well as polyamino propane sulfonic acid (AMPS), zinc citrate trihydrate, polypeptides (such as polyaspartic and polyglutamic acids), and mixtures thereof.

Chelating Agents

The compositions may include a chelating agent. Chelating agents include tartaric acid and pharmaceutically-acceptable salts thereof, citric acid and alkali metal citrates and mixtures thereof. Chelating agents may complex calcium found in the cell walls of the bacteria. Chelating agents may also disrupt plaque by removing calcium from the calcium bridges which help hold this biomass intact. A chelating agent that may result in tooth demineralization should not be used.

In some embodiments, alkali metal citrates (e.g., sodium and potassium citrate) are present in the compositions. In certain cases, chelating agents include a citric acid/alkali metal citrate combination. In other cases, alkali metal salts of tartaric acid may be used. Other agents include disodium tartrate, dipotassium tartrate, sodium potassium tartrate, sodium hydrogen tartrate and potassium hydrogen tartrate. The tartaric acid salt chelating agent may be used alone or in combination with other optional chelating agents. In certain embodiments, these chelating agents have a calcium binding constant of about $10^1$ to $10^5$ to provide improved cleaning with reduced plaque formation.

Another group of chelating agents is the anionic polymeric polycarboxylates. Such materials are well known in the art, being employed in the form of their free acids, partially or fully neutralized water soluble alkali metal (e.g. potassium and preferably sodium) or ammonium salts. In certain cases, composition contain 1:4 to 4:1 copolymers of maleic anhydride or acid with another polymerizable ethylenically unsaturated monomer, such as methyl vinyl ether (methoxyethylene) having an average molecular weight (AMW) of about 30,000 to about 1,000,000.

Other operative polymeric polycarboxylates may include those such as the 1:1 copolymers of maleic anhydride with ethyl acrylate, hydroxyethyl methacrylate, N-vinyl-2-pyrrolidone, or ethylene, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates may be copolymers of maleic anhydride with styrene, isobutylene or ethyl vinyl ether, polyacrylic, polyitaconic and polymaleic acids, and sulfoacrylic oligomers of AMW as low as 1,000.

The amounts of chelating agent may be about 0.1% to about 2.5%, about 0.5% to about 2.5%, or from about 1.0% to about 2.5%.

Fluoride Source

In certain embodiments, a water-soluble fluoride compound may be present in an oral care composition in an amount sufficient to give a fluoride ion concentration in the composition at 25° C., from about 0.0025% to about 5.0% by weight, or about 0.005% to about 2.0% by weight. A wide variety of fluoride ion-yielding materials may be employed as sources of soluble fluoride in the present compositions. Representative fluoride ion sources may include stannous fluoride, sodium fluoride, potassium fluoride, sodium monofluorophosphate and many others. In certain cases, the subject composition contain stannous fluoride and sodium fluoride, as well as mixtures thereof.

Teeth Whitening Actives and Teeth Color Modifying Substances

A teeth whitening agent and/or teeth color-modifying substance may also be present in the oral care compositions. These substances are suitable for modifying the color of the teeth. These substances may comprise particles that when applied on the tooth surface modify that surface in terms of absorption and, or reflection of light. Such particles may provide an appearance benefit when a film containing such particles is applied over the surfaces of a tooth or teeth.

Particles include pigments and colorants routinely used in the cosmetic arts. There are no specific limitations as to the pigment and, or colorant used in the present composition. Pigments and colorants include inorganic white pigments, inorganic colored pigments, pearling agents, filler powders and the like. Specific examples may be selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In certain embodiments, titanium dioxide, bismuth oxychloride, zinc oxide, or mixtures thereof are used.

The pigments may be used as opacifiers and colorants. These pigments may be used as treated particles, or as the raw pigments themselves. Typical pigment levels may to be selected for the particular impact that is desired by the consumer. For example, for teeth that are particularly dark or stained one may use pigments in sufficient amount to lighten the teeth. On the other hand, where individual teeth or spots on the teeth are lighter than other teeth, pigments to darken the teeth may be useful. The levels of pigments and colorants may be used in the range of about 0.05% to about 20%, from about 0.10% to about 15%, or from about 0.25% to about 10% of the composition.

Thickening Agents

In certain embodiments, such as toothpaste or gels, some thickening material may provide a consistency of the composition, active release characteristics upon use, shelf stability, and stability of the composition, etc. Thickening agents include carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums, such as gum karaya, xanthan gum, gum arabic, and gum tragacanth, may also be used. Colloidal magnesium aluminum silicate or finely divided silica may be used as part of the thickening agent to further improve texture.

Thickening or gelling agents may include a class of homopolymers of acrylic acid crosslinked with an alkyl ether of pentaerythritol or an alkyl ether of sucrose, or carbomers, or mixtures thereof.

Copolymers of lactide and glycolide monomers having a molecular weight in the range of from about 1,000 to about 120,000 (number average), may be used in the subject composition such as a "subgingival gel."

Thickening agents may be used in an amount from about 0.1% to about 15%, about 2% to about 10%, or from about 4% to about 8%, by weight of the total toothpaste or gel composition. Higher concentrations may be used for chewing gums, lozenges (including breath mints), sachets, non-abrasive gels and subgingival gels.

Humectants

In certain embodiments, topical, oral carrier of the subject composition may include a humectant. The humectant may serve to keep the subject compositions from hardening upon exposure to air, to give compositions a moist feel to the mouth, and, for particular humectants, to impart desirable sweetness of flavor to toothpaste compositions. The humectant, on a pure humectant basis, may comprise from about 0% to about 70%, or about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol. In certain cases, the humectant is sorbitol and/or glycerin.

Flavoring and Sweetening Agents

Flavoring agents may also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents may be used in the compositions at levels of from about 0.001% to about 5%, by weight of the composition.

Suitable sweetening agents include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame, cyclamate salts, sodium cyclamate or sodium saccharin, and mixtures thereof. A composition may contain from about 0.1% to about 10% of these agents, or from about 0.1% to about 1%, by weight of the composition.

In addition to flavoring and sweetening agents, coolants, salivating agents, warming agents, and numbing agents may be used as optional ingredients in the subject composition. These agents may be present in the compositions at a level of from about 0.001% to about 10%, or from about 0.1% to about 1%, by weight of the composition.

The coolant may be any of a wide variety of materials. Included among such materials are carboxamides, menthol, ketals, diols, and mixtures thereof. Exemplary coolants are paramenthan carboxyamide agents such as N-ethyl-p-menthan-3-carboxamide, N,2,3-trimethyl-2-isopropylbutanamide, and mixtures thereof. Other coolants may be selected from the group consisting of menthol, 3-1-menthoxypropane-1,2-diol, menthone glycerol acetal, and menthyl lactate. The terms menthol and menthyl include dextro- and levorotatory isomers of these compounds and racemic mixtures, thereof.

Warming agents include *capsicum* and nicotinate esters, such as benzyl nicotinate. Numbing agents may include benzocaine, lidocaine, clove bud oil, and ethanol.

Alkali Metal Bicarbonate Salt

The compositions may also include an alkali metal bicarbonate salt. Alkali metal bicarbonate salts may be soluble in water and unless stabilized, may release carbon dioxide to in an aqueous system. Sodium bicarbonate, also known as baking soda, may be present as the alkali metal bicarbonate salt. In certain embodiments, the composition contains from about 0.5% to about 30%, about 0.5% to about 15%, or from about 0.5% to about 5% of an alkali metal bicarbonate salt.

Miscellaneous Carriers

Water employed in the preparation of the oral care compositions may be of low ion content and free of organic impurities, and may be present in an amount of about 5% to about 70%, or from about 20% to about 50%, by weight, of an aqueous composition. These amounts of water may include free water that is added, plus water that is introduced with other agents or carriers.

Poloxamers may be employed in the compositions. The poloxamer may be classified as a nonionic surfactant. It may function as an emulsifying agent, binder, or stabilizer, or perform a related function. Poloxamers include difunctional block-polymers terminating in primary hydroxyl groups with molecular weights ranging from 1,000 to above 15,000.

Other emulsifying agents that may be used in the compositions include polymeric emulsifiers. Predominantly high molecular weight polyacrylic acid polymers may be useful as emulsifiers.

Titanium dioxide may also be added to the composition. Titanium dioxide is a white powder which may add opacity to the compositions. Titanium dioxide may comprise from about 0.25% to about 5% by weight of the composition.

The pH of the composition is preferably adjusted through the use of one or more buffering agents. Buffering agents refer to agents that can be used to adjust the pH of the compositions in a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents may be administered at a level of from about 0.5% to about 10%, by weight of the present compositions. In certain embodiments, the pH of dentifrice compositions may be measured from a 3:1 aqueous slurry of dentifrice, e.g., 3 parts water to 1 part dentifrice.

Other agents that may be used in the present compositions include dimethicone copolyols selected from alkyl- and alkoxy-dimethicone copolyols, such as C12 to C20 alkyl dimethicone copolyols and mixtures thereof. In certain cases, the compositions to contain cetyl dimethicone copolyol. The dimethicone copolyol may be present in a level of from about 0.01% to about 25%, about 0.1% to about 5%, or from about 0.5% to about 1.5% by weight. The dimethicone copolyols may aid in providing positive tooth feel benefits.

Other Active Agents

The present oral care composition may also include other active agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. Water soluble antimicrobials include quaternary ammonium salts and bis-biquamide salts, among others. An additional water soluble antimicrobial agent is triclosan monophosphate. Quaternary ammonium agents include those in which one or two of the substitutes on the quaternary nitrogen has a carbon chain length (typically alkyl group) from about 8 to about 20, or from about 10 to about 18 carbon atoms while the remaining substitutes (typically alkyl or benzyl group) have a lower number of carbon atoms, such as from about 1 to about 7 carbon atoms, such as methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethylhexyl)-5-methyl-hexahydropyrimidine, benzalkonium chloride, benzethonium chloride and methyl benzethonium chloride are exemplary of quaternary ammonium antibacterial agents. Other compounds are bis[4-(R-amino)-1-pyridinium]alkanes. Other antimicrobials, such as copper bisglycinate, copper glycinate, zinc citrate, and zinc lactate, may also be included.

In addition to an α-glucanase, the present oral care compositions may also contain one or more other enzymes that have carbohydrate hydrolysis, antimicrobial, or teeth whitening activity. Such enzymes include, but are not limited to, a deaminase, an esterase, a glycosidase, glucanhydrolase, a dextrinase, an amylase, a transglucosidase, a cellulase, a hemicellulase, a lipase, an oxidase, a peroxidase, a protease, and a urease.

C. Method of Use

Another aspect of the present compositions and method is a method of contacting a tooth surface with a composition comprising an alpha-glucanase to reduce or prevent tooth decay, or to reduce or prevent the underlying causes of tooth decay.

In some embodiments, the method involves contacting a tooth surface with a composition comprising an alpha-glucanase to hydrolyze a glycocalyx present on the tooth surface. According to this embodiment, the 1,3-α-D-glucosidase activity of the alpha-glucanase, and/or other activities of the alpha-glucanase, hydrolyzes polysaccharides, glucans, mannans, and/or adhesive molecules produced by plaque bacteria, thereby decreasing the ability of plaque to adhere to the tooth surface, reducing plaque formation or reducing the levels of existing plaque. Such polysaccharides, glucans, mannans, and/or adhesive molecules may be present in what is conventionally referred to as the glycocalyx.

In some embodiments, the method involves contacting a tooth surface with a composition comprising an alpha-glucanase to dewater the tooth surface by disrupting the polysaccharides, glucans, mannans, and/or adhesive molecules produced by bacteria in the mouth, thereby reducing film formation or bacterial adhesion, and/or preventing the accumulation of bacterial acids and other substances that damage the tooth surface.

The method may include contacting the tooth surface with one or more alpha-glucanases, which may be formulated as described, above. The methods may include contacting the tooth surface with an additional enzyme, which may be present in the same formulation or a different formulation. In some embodiments, the enzyme is a deaminase, an esterase, a glycosidase, glucanhydrolase, a dextrinase, an amylase, a transglucosidase, a cellulase, a hemicellulase, a lipase, an oxidase, a peroxidase, a protease, and a urease. The additional enzyme may also be an additional alpha-glucanase.

Tooth and other personal care compositions and their mechanisms of action are described in detail in Lad. R. (ed.) "Biotechnology in Personal Care", *Cosmetic Science and Technology Series, Vol.* 29, Taylor and Francis Group, New York, N.Y., USA, 2006. This reference is indicative of the state of the art, as is incorporated herein.

In addition to oral care applications, the present compositions and methods can be adapted for the prevention or removal of biofilms in a large number of other situations, for example, in cooling water equipment, in drinking water equipment, in food products and food handling equipment, on (or in) medical implants, in paper and textile manufacturing and processing, in oil refinery and mining equipment, on the hulls of ships to and boats, in chemical manufacturing, in swimming pools, aquariums, and ponds, and the like. In such cases, alpha glucanases can be used to disrupt polysaccharide components present in the biofilm, thereby reducing the attachment and/or adhesion of microorganism to surfaces. The disruption of such polysaccharides also results in dewatering, which reduces or prevents the formation of a microenvironment suitable for the growth and propagation of microorganism on a surface.

Other aspects and embodiments of the present compositions and methods will be apparent to the skilled person in view of the disclosure.

EXPERIMENTAL

The following examples are offered to illustrate the present compositions and methods, and advantages thereof, and should not be construed as limiting their scope.

Example 1

Identification of Candidate Fungal α-1,3-glucanases (EC 3.2.1.59)

Several candidate fungi, including *Hypocrea tawa, Trichoderma reesei, Trichoderma konilangbra*, and *Trichoderma harzianum* were grown in culture in defined media with 15% maltose (28° C., 7 days, 150 rpm agitation). Supernatants were harvested by sterile filtration, concentrated, and desalted for glucan (and dextran) hydrolysis activity screening. The desalted culture supernatants (5% by volume) were added to 0.2% washed insoluble glucan in 100 mM phosphate buffer, pH 6.3 (or 100 mM acetate buffer, pH 4.5). The reaction mixtures were incubated overnight at 37-40° C. . The mixtures were visually inspected for solubilization of the insoluble glucan, and the supernatants were analyzed by HPLC for soluble hydrolysis products. For HPLC analysis, the reaction supernatant was diluted 10-fold into 10 mM NaOH, and 10 µl was then injected into an Agilent 1100 HPLC equipped with electrochemical detection. Mono- and disaccharides were eluted with a NaOH/sodium acetate gradient on a PA1 anion exchange column. The components of unknown mixtures were identified based on previously run standards. The supernatants from the *Trichoderma reesei, Trichoderma konilangbra*, and *Hypocrea tawa* resulted in the most solubilization of glucan (see, e.g., FIG. 2). The α-1,3-glucanases of *H. tawa, T. reesei*, and *T. konilangbra* were selected for cloning, expression, and characterization. Putative *T. reesei* α-1,3-glucanase sequences were identified in the genome sequence (JGI) by homology.

Example 2

Isolation of Genomic DNA

Fungal cultures of *T. reesei, T. konilangbra*, and *H. tawa* were prepared by adding 30 mL of sterile YEG broth to three 250 mL baffled Erlenmeyer shaking flasks in the biological hood. A 1×1 inch square was cut and removed from each respective fungal culture plate using a sterile plastic loop and placed into the appropriate culture flask. The inoculated flasks were then placed into the 28° C. shaking incubator to grow overnight.

The *T. reesei, T. konilangbra, H. tawa* cultures were removed from the shaking incubator and the contents of each flask were poured into separate sterile 50 mL Sarstedt tubes. The Sarstedt tubes were placed in a table-top centrifuge and spun at 4,500 rpm for 10 minutes to pellet the fungal mycelia. The supernatants were discarded and a large loopful of each mycelial sample was transferred to a separate tube containing lysing matrix (FastDNA). Genomic DNA was extracted from the harvested mycelia using the FastDNA kit (Qbiogene), according to the manufacturer's protocol for algae, fungi and yeast. The homogenization time (Mini BeadBeater-8) was 25 seconds. The amount and quality of genomic DNA extracted was determined by gel electrophoresis.

Example 3

Obtaining Alpha-Glucanase Polypeptides by PCR

A. *T. reesei*

Putative α-1,3 glucanase genes were identified in the *T. reesei* genome (JGI) by homology. PCR primers for *T. reesei* were designed based on the putative homolog DNA sequences. Degenerate PCR primers were designed for *T. konilangbra* or *H. tawa* based on the putative *T. reesei* protein sequences and other published α-1,3 glucanase protein sequences.

*T. reesei* specific PCR primers:

```
SK592: 5' - CACCATGTTTGGTCTTGTC-      (SEQ ID NO: 6)
CGC

SK593: 5' - TCAGCAGTACTGGCATGCTG      (SEQ ID NO: 7)
```

The PCR conditions used to amplify the putative α-1,3 glucanase from genomic DNA extracted from *T. reesei* strain RL-P37 were as follows: 1. 94° C. for 2 minutes, 2. 94° C. for 30 seconds, 3. 56° C. for 30 seconds, 4. 72° C. for 3 minutes, 5. return to step 2 for to 24 cycles, 6. 4° C. indefinitely. Reaction samples contained 2 µL of RL-P37 genomic DNA, 10 µL of the 10× buffer, 2 µL 10 mM dNTPs mixture, 1 µL primers SK592 and SK593 at 20 µM, 1 µL of the Pfu Ultra and 83 µL distilled water.

B. *T. konilangbra* and *H. tawa*

Initial PCR reactions used degenerate primers designed from protein alignments of several homologous sequences. A primary set of degenerate primers, designed to anneal near the 5' and 3' ends, were used in the first PCR reaction to amplify similar sequences to that of an α-1,3 glucanase.

Degenerate Primers for Initial Cloning:

```
H. tawa and T. konilangbra:
MA1F:
GTNTTYTGYCAYTTYATGAT                  (SEQ ID NO: 8)

MA2F:
GTNTTYTGYCAYTTYATGATHGGNAT            (SEQ ID NO: 9)

MA4F:
GAYTAYGAYGAYGAYATGCARCG               (SEQ ID NO: 10)
```

-continued

```
MA5F:
GTRCAYTTRCAIGGICCIGGIGGRCARTANCC        (SEQ ID NO: 11)

MA6R:
YTCICCIGGNAGNGGRCANCCRTT                (SEQ ID NO: 12)

MA7R:
RCARTAYTGRCAIGCYGTYGGYGGRCARTA          (SEQ ID NO: 13)
```

The products of these PCR reactions were then used in a nested PCR, using primers designed to attach within the product of the initial PCR fragment, under the same amplification conditions.

Specific Primers for Initial Cloning:

```
T. konilangbra:
TP1S: CCCCCTGGCCAAGTATGTGT              (SEQ ID NO: 14)

TP2A: GTACGCAAAGTTGAGCTGCT              (SEQ ID NO: 15)

TP3S: AGCACATCGCTGATGGATAT              (SEQ ID NO: 16)

TP3A: AAGTATACGTTGCTTCCGGC              (SEQ ID NO: 17)

TP4S: CTGACGATCGGACTRCACGT              (SEQ ID NO: 18)

TP4A: GGTTGTCGACGTAGAGCTGT              (SEQ ID NO: 19)

H. tawa:
HP2A: ACGATCGGCAGAGTCATAGG              (SEQ ID NO: 20)

HP3S: ATCGGATTGCATGTCACGAC              (SEQ ID NO: 21)

HP3A: TACATCCAGACCGTCACCAG              (SEQ ID NO: 22)

HP4S: ACGTTTGCTCTTGCGGTATC              (SEQ ID NO: 23)

HP4A: TCATTATCCCAGGCCTAAAA              (SEQ ID NO: 24)
```

Gel electrophoresis of the PCR products was used to determine whether fragments of expected size were amplified. Single nested PCR products of the expected size were purified using the QIAquick PCR purification kit (Qiagen). In addition, expected size products were excised and extracted from agarose gels containing multiple product bands and purified using the QIAquick Gel Extraction kit (Qiagen).

Example 4

Transformation/Isolate Screening/Plasmid Extraction

PCR products were inserted into cloning vectors using the Invitrogen Zero Blunt® TOPO® PCR Cloning Kit, according to the manufacturer's specifications. The vector was then transformed into One° Shot Top 10 chemically competent *E. coli* cells (Invitrogen), according to the manufacturer's recommendation and then spread onto LB plates containing 50 ppm of Kanamycin. These plates were incubated in the 37° C. incubator overnight.

To select transformants that contained the vector and DNA insert, colonies were selected from the plate for crude plasmid extraction. 50 µL of DNA Extraction Solution (100 mM NaCl, 10 mM EDTA, 2 mM Tris pH 7) was added to clean 1.5 mL Eppendorf tubes. In the biological hood, 7-10 individual colonies of each TOPO® transformation clone were numbered, picked and resuspended in the extraction solution. In the chemical hood, 50 µL of Phenol: Chloroform: Isoamyl alcohol was added to each sample and vortexed thoroughly. Tubes were microcentrifuged at maximum speed for 5 minutes, after which 20 µL of the top aqueous layer was removed and placed into a clean PCR tubes. 1 µL of RNase 2 mg/mL was then added, and samples were mixed and incubated at 37° C. for 30 minutes. The entire sample volume was then run on a gel to determine the presence of the insert in the TOPO® vector based on difference in size to an empty vector. Once the transformant colonies had been identified, those clones was scraped from the plate, and used to inoculate separate 15 mL tubes containing 5 ml of LB/Kanamycin medium (0.0001%). The cultures were placed in the 37° C. shaking incubator overnight.

Samples were removed from the incubator and centrifuged for 6 minutes at 6,000 rpm using the Sorval centrifuge. The QIAprep Spin Miniprep kit (Qiagen) and protocol were used to isolate the plasmid DNA, which was then digested to confirm the presence of the insert. The restriction enzyme used was dependent on the sites present in and around to the insert sequence. Gel electrophoresis was used to determine fragment size. Appropriate DNA samples were submitted for sequencing (Sequetech, Mountain View, Calif.).

Example 5

Cloning the 3' and 5' Ends

All DNA fragments were sequenced. Sequences were aligned and compared to determine nucleotide and amino acid identities using Align X and ContigExpress® (Vector NTI® suite, Invitrogen). Specific primers were designed to amplify the 3' and 5' portions of each incomplete fragment from *H. tawa* and *T. konilangbra* by extending outward from the known sequence. At least three specific primers, each nested within the amplified product of the previous primer set, were designed for each template. Amplification of the 5' and 3' sequences was performed using the nested primer sets with the LA PCR In vitro Cloning Kit (TaKaRa BIO Inc.).

Fresh genomic DNA was prepared for this amplification. Cultures of *T. konilangbra* and *H. tawa* were prepared by inoculating 30 mL of YEG broth with a 1 square inch section of the appropriate sporulated fungal plate culture in 250 mL baffled Erlenmeyer flasks. The flasks were incubated in the 28° C. shaking incubator overnight. The cultures were harvested by centrifugation in 50 mL Sarstedt tubes at 4,500 rpm for 10 minutes. The supernatant was discarded and the mycelia were stored overnight in a −80° C. freezer. The frozen mycelia were then placed into a coffee grinder along with a few pieces of dry ice. The grinder was run until the entire mixture had a powder-like consistency. The powder was then air dried and transferred to a sterile 50 mL Sarstedt tube containing 10 mL of Easy-DNA™ Kit Solution A (Invitrogen) and the manufacturer's protocol was followed. The concentration of the genomic DNA collected from the extraction was measured using the NanoDrop spectrophotometer.

The LA PCR In vitro Cloning Kit cassettes were chosen based on the absence of a particular restriction site within the known DNA sequences, and the manufacturer's instructions were followed. For first PCR run, 1 µL of the ligation DNA sample was diluted in 33.5 µL of sterilized distilled water. Different primers were used depending on the sample and the end fragment desired. For the 5' ends, primers HP4A and TP3A were used for *H. tawa* and *T. konilangbra* respectively, while for the 3' ends primers HP4S and TP3S were used for *H. tawa* and *T. konilangbra*. The PCR mixture was prepared by to adding 34.5 µL diluted ligation DNA solution, 5 µL of 10×LA Buffer II ($Mg^{+2}$), 8 µL dNTPs mixture, 1 µL cassette primer I, 1 µL specific primer I (depending on sample and end fragment), and 0.5 µL TaKaRa LA Taq. The PCR tubes were then placed in a thermocycler following the listed protocol: 1.

94° C. for 10 minutes, 2. 94° C. for 30 seconds, 3. 55° C. for 30 seconds, 4. 72° C. for 4 minutes, return to step 2. 30 times, 4° C. indefinitely.

A second PCR reaction was prepared by taking 1 µL of the first PCR reaction and diluting the sample in sterilized distilled water to a dilution factor of 1/10,000. A second set of primers nested within the first amplified region were used to amplify the fragment isolated in the first PCR reaction. Primers HP3A and TP4A were used to amplify toward the 5' end of *H. tawa* and *T. konilangbra* respectively, while primers HP3S and TP4S were used to amplify toward the 3' end. The diluted DNA was added to the PCR reaction containing 33.5 µL distilled sterilized water, 5 µL 10×LA Buffer II ($Mg^{+2}$), 8 µL dNTPs mixture, 1 µL of cassette primer 2, 1 µL of specific primer 2 (dependent on sample and fragment end), 0.5 µL TaKaRa LA Taq, and mixed thoroughly before the PCR run. The PCR protocol was the same as the first reaction, without the initial 94° C. for 10 minutes. After the reaction was complete, the sample was run by gel electrophoresis to determine size and number of fragments isolated. If a single band was present, the sample was purified and sent for sequencing. If no fragment was isolated, a third PCR reaction was performed using the previous protocol for a nested PCR reaction. After running the amplified fragments by gel electrophoresis, the brightest band was excised, purified, and sent for sequencing.

Example 6

Analysis of Sequence Alignments

Sequences were obtained and analyzed using the Vector NTI suite, including Align X, and ContigExpress. Each respective end fragment sequence was aligned to the previously obtained fragments of *H. tawa* and *T. konilangbra* to obtain the entire gene sequence. Nucleotide alignments with *T. harzianum* and *T. reesei* sequences revealed the translation start and stop points of the gene of interest in both *H. tawa* and *T. konilangbra*. After the entire gene sequence was identified, specific primers were designed to amplify the entire gene from the genomic DNA. Primers were designed as described earlier, with to the exception of adding CACC nucleotide sequence before the translational starting point, for GATEWAY° cloning (Invitrogen).
Primers for Final Cloning:

```
T. konilangbra:
T1FS: caccatgctaggcattctccg        (SEQ ID NO: 25)

T1FA: tcagcagtattggcatgccg         (SEQ ID NO: 26)

H. tawa:
H1FS: CACCATGTTGGGCGTTTTTCG        (SEQ ID NO: 27)

H1FA: CTAGCAGTATTGRCATGCCG         (SEQ ID NO: 28)
```

The PCR protocol was followed as previously described with the exception of altering the annealing temperature to 55° C. After a single band was isolated and viewed through gel electrophoresis, the amplified fragment was purified as described earlier and used in the pENTR/D TOPO® (Invitrogen) transformation, according to the manufacturer's instructions. Chemically competent *E. coli* were then transformed as previously described, and transferred to LB plates containing 50 ppm of kanamycin. Following 37° C. incubation overnight, transformants containing the plasmid and insert were selected after crude DNA extraction and plasmid size analysis, as previously described. The selected transformants were scraped from the plate and used to inoculate a fresh 15 mL tube containing 5 ml of LB/Kanamycin medium (0.0001%). Cultures were placed in the 37° C. shaking incubator overnight. Cells were harvested by centrifugation and the plasmid DNA extracted as previously described. Plasmid DNA was digested to confirm the presence of the insert sequence, and then submitted for sequencing. The LR Clonase reaction (Gateway Cloning, Invitrogen) was used, according to manufacturer's instructions, to directionally transfer the insert from the pENTR/D vector into the destination vector. The destination vector is designed for expression of a gene of interest, in *T. reesei*, under control of the CBH1 promoter and terminator, with *A. niger* acetamidase for selection.

Example 7

Biolistic Transformation

A *T. reesei* spore suspension was spread onto the center ~6 cm diameter of an acetamidase transformation plate (150 µL of a $5 \times 10^7$-$5 \times 10^8$ spore/mL suspension). The plate was then air dried in a biological hood. The stopping screens (BioRad 165-2336) and the macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165-2335) was placed flatly on top of the filter paper and the Petri dish lid replaced.

A tungsten particle suspension was prepared by adding 60 mg tungsten M-10 particles (microcarrier, 0.7 micron, BioRad #1652266) to an Eppendorf tube. 1 mL ethanol (100%) was added. The tungsten was vortexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 mL of sterile 50% glycerol.

The transformation reaction was prepared by adding 25 µL suspended tungsten to a 1.5 mL Eppendorf tube for each transformation. Subsequent additions were made in order, 2 µL DNA pTrex3g expression vectors, 25 µL 2.5M $CaCl_2$, 10 µL 0.1M spermidine. The reaction was vortexed continuously for 5-10 minutes, keeping the tungsten suspended. The Eppendorf tube was the microfuged briefly and decanted. The tungsten pellet was washed with 200 µL of 70% ethanol, microfuged briefly to pellet and decanted. The pellet was washed with 200 µL of 100% ethanol, microfuged briefly to pellet, and decanted. The tungsten pellet was resuspended in 24 µL 100% ethanol. The Eppendorf tube was placed in an ultrasonic water bath for 15 seconds and 8 µL aliquots were transferred onto the center of the desiccated macrocarriers. The macrocarriers were left to dry in the desiccated Petri dishes.

A Helium tank was turned on to 1500 psi. 1100 psi rupture discs (BioRad 165-2329) were used in the Model PDS-1000/He Biolistic Particle Delivery System (BioRad). When the tungsten solution was dry, a stopping screen and the macrocarrier holder were inserted into the PDS-1000. An acetamidase plate, containing the target *T. reesei* spores, was placed 6 cm below the stopping screen. A vacuum of 29 inches Hg was pulled on the chamber and held. The He Biolistic Particle Delivery System was fired. The chamber was vented and the acetamidase plate removed for incubation at 28° C. until colonies appeared (5 days).

| Modified amdS Biolistic agar (MABA) | per liter | |
| --- | --- | --- |
| Part I, make in 500 ml dH$_2$O | | |
| 1000x salts | 1 | ml |
| Noble agar | 20 | g |
| pH to 6.0, autoclave | | |
| Part II, make in 500 ml dH$_2$O | | |
| Acetamide | 0.6 | g |
| CsCl | 1.68 | g |
| Glucose | 20 | g |
| KH$_2$PO$_4$ | 15 | g |
| MgSO$_4$•7H$_2$O | 0.6 | g |
| CaCl$_2$•2H$_2$O | 0.6 | g | pH to 4.5, 0.2 micron filter sterilize; leave in 50° C. oven to warm, add to agar, mix, pour plates. Stored at room temperature.

| 1000x Salts | per liter |
| --- | --- |
| FeSO$_4$•7H$_2$O | 5 g |
| MnSO$_4$•H$_2$O | 1.6 g |
| ZnSO$_4$•7H$_2$O | 1.4 g |
| CoCl$_2$•6H$_2$O | 1 g |
| Bring up to 1 L dH$_2$O. | |
| 0.2 micron filter sterilize | |

Example 8

Expression of α-1,3 glucanases by *T. reesei* Transformants

A 1 cm$^2$ agar plug was used to inoculate Proflo seed media. Cultures were incubated at 28° C., with 200 rpm shaking. On the second day, a 10% transfer was aseptically made into Production media. The cultures were incubated at 28° C., with 200 rpm shaking On the third day, cultures were harvested by centrifugation. Supernatants were sterile-filtered (0.2 μm PES) and stored at 4° C. Analysis by SDS-PAGE identified clones expressing the respective alpha-glucanase genes.

Example 9

Preparation of Insoluble Glucan Substrate

Four sterile flasks containing BHI (brain heart infusion) broth were inoculated with *Streptococcus sobrinus* (ATCC 27607), from a BHI plate. The cultures were incubated at 37° C. for 24 hrs, static, after which they were visibly turbid. The supernatants (containing the *S. sobrinus* glucosyltransferases) were harvested by centrifugation (15 minutes, 10,000 to rpm). The supernatants were pooled and sterile-filtered (0.22 μm) to remove any remaining cells. Aseptically, sucrose was added to a final concentration of 5%, which induces the glucosyltransferases to produce glucan polymer. The culture supernatant plus sucrose was sealed, mixed, and stored at 37° C. incubator for 24-48 hrs (static). A fluffy precipitate formed and was harvested by centrifugation (10, 000 rpm, 15 minutes). The supernatant was decanted, leaving the precipitate, which was washed with dI water three times, lastly in a tared Eppendorf tube. The glucan was dried in a SpeedVac, and the Eppendorf weight was recorded after drying.

Example 10

PAHBAH Reducing Sugars Assay to Measure the Activity of Cloned Alpha-Glucanases

Transformed *T. reesei* culture supernatants, buffer and insoluble glucan were distributed into a round-bottom 96-well plate in the amounts listed below. Two types of buffers (pH 4.5 and pH 6.0) were used to compare activity levels. After the samples were distributed, the 96-well plate was sealed and placed into a shaking 37° C. incubator overnight.

Glucan hydrolysis mixture:
50 μL culture supernatant
50 μL of a 28 mg/mL glucan solution
5 μL 1M Citrate buffer (pH 4.5 or 6.0)
105 μL PAHBAH solution:
0.5 g Sodium potassium tartrate
0.15 g p-hydroxybenzoic acid hydrazide (PAHBAH)
10 mL 2% NaOH Following incubation, 150 μL of freshly made PAHBAH (p-hydroxybenzoic acid hydrazide) reagent was transferred into 0.2 mL PCR tubes along with 20 μL of each hydrolysis mixture. These tubes were then lightly mixed and placed into a thermocycler, where they were heated to 99° C. for 30 minutes. The PCR tubes were removed and 150 μL of each sample was transferred to a fresh 96-well plate. The absorbance of each sample was measured at 410 nm. Results of this assay are shown in FIG. 3.

What is claimed is:

1. A method for making an oral care composition for the removal of biofilms, comprising:
   admixing an α-glucanase having an amino acid sequence that is at least 90% identical to that of mature *Trichoderma reesei* α-glucanase (amino acid residues 38-622 of SEQ ID NO: 2) with an orally acceptable excipient to make an oral care composition for the, thereby removing biofilms.

2. The method of claim 1, further comprising:
   packaging said oral care composition.

3. A method for reducing dental plague comprising: contacting the oral care composition of claim 1 comprising the α-glucanase with a tooth in a mouth under conditions suitable for activity of said α-glucanase, wherein said contacting of the oral composition reduces dental plague.

4. The method of claim 3, wherein the oral care composition is contacted with the tooth by a toothbrush.

5. A method for removing biofilms, comprising:
   contacting a composition comprising an α-glucanase having an amino acid sequence that is at least 90% identical to that of mature *Trichoderma reesei* α-glucanase (amino acid residues 38-622 of SEQ ID NO: 2) with a biofilm under conditions suitable for activity of said α-glucanase to disrupt polysaccharide components present in the biofilm, thereby removing biofilms.

6. The method of claim 5, wherein the biofilm is present in or on cooling water equipment, drinking water equipment, food handling equipment, medical implants, paper and textile manufacturing equipment, oil refining or mining equipment, a hull of a ship or boat, chemical manufacturing equipment, a swimming pool, an aquarium, or a pond.

7. The method of claim 5, wherein the biofilm is present on a tooth.

8. The method of claim 7, wherein said contacting is performed using a toothbrush.

9. The method of claim 7, wherein said method results in prevention and/or reduction in dental plaque.

* * * * *

UNITED STATES PATENT AND TRADEMARK OFFICE
CERTIFICATE OF CORRECTION

PATENT NO. : 8,709,386 B2  
APPLICATION NO. : 12/937362  
DATED : April 29, 2014  
INVENTOR(S) : Kim et al.

Page 1 of 1

It is certified that error appears in the above-identified patent and that said Letters Patent is hereby corrected as shown below:

In the Claims

Claim 3, column 67, lines 35 and 39, delete "plague" and insert --plaque--.

Claim 9, column 68, line 42, delete "prevention and/or".

Signed and Sealed this  
Fourth Day of November, 2014

Michelle K. Lee  
*Deputy Director of the United States Patent and Trademark Office*